United States Patent
Nguyen

(10) Patent No.: US 12,402,897 B2
(45) Date of Patent: *Sep. 2, 2025

(54) SYSTEM FOR TREATING THROMBUS IN BODY LUMENS

(71) Applicant: Shockwave Medical, Inc., Santa Clara, CA (US)

(72) Inventor: Hoa Nguyen, Santa Clara, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 329 days.

This patent is subject to a terminal disclaimer.

(21) Appl. No.: 17/948,528

(22) Filed: Sep. 20, 2022

(65) Prior Publication Data

US 2023/0011207 A1     Jan. 12, 2023

Related U.S. Application Data

(63) Continuation of application No. 17/025,866, filed on Sep. 18, 2020, now Pat. No. 11,478,261.
(Continued)

(51) Int. Cl.
     *A61B 17/22*      (2006.01)

(52) U.S. Cl.
     CPC .......... *A61B 17/22004* (2013.01); *A61B 2017/22007* (2013.01); *A61B 2017/22042* (2013.01); *A61B 2217/007* (2013.01)

(58) Field of Classification Search
     CPC ............ A61B 17/22; A61B 17/22004; A61B 17/22012; A61B 17/22022; A61B 17/225;
(Continued)

(56) References Cited

U.S. PATENT DOCUMENTS

| 2,916,647 A | 12/1959 | George |
| 3,051,862 A | 8/1962 | Hoff |

(Continued)

FOREIGN PATENT DOCUMENTS

| AU | 2009313507 B2 | 11/2014 |
| AU | 2013284490 B2 | 5/2018 |

(Continued)

OTHER PUBLICATIONS

21 C.F.R. 870.5100 Title 21, vol. 8 Apr. 1, 2018, 2 pages.
(Continued)

*Primary Examiner* — Robert A Lynch
(74) *Attorney, Agent, or Firm* — Morrison & Foerster LLP

(57) ABSTRACT

The present disclosure relates generally to thrombectomy devices. An exemplary catheter comprises: an emitter assembly comprising at least one emitter; wherein each emitter comprises an electrode pair, and wherein each emitter is configured to generate a plurality of cavitation bubbles when a voltage is applied to the pair of electrodes; an infusion lumen formed by at least a portion of an outer wall of the catheter, the infusion lumen configured to receive a conductive fluid, wherein the emitter assembly is housed within the infusion lumen, wherein a distal segment of the infusion lumen includes a plurality of holes on the portion of the outer wall of the catheter, and wherein the plurality of holes are configured to release the conductive fluid and the plurality of cavitation bubbles out of the catheter to treat thrombus at a treatment site; an aspiration lumen including aspiration ports at the distal segment thereof.

24 Claims, 4 Drawing Sheets

Related U.S. Application Data

(60) Provisional application No. 62/904,974, filed on Sep. 24, 2019.

(58) Field of Classification Search
CPC .... A61B 17/32037; A61B 2017/22005; A61B 2017/22007; A61B 2017/22008; A61B 2017/22025; A61B 2017/22042; A61B 2017/22084; A61B 2017/22089; A61B 2017/22091; A61B 2017/22094; A61B 2217/005; A61B 2217/007
See application file for complete search history.

(56) References Cited

U.S. PATENT DOCUMENTS

| | | |
|---|---|---|
| 3,412,288 A | 11/1968 | Ostrander |
| 3,413,976 A | 12/1968 | Roze |
| 3,524,101 A | 8/1970 | Barbini |
| 3,583,766 A | 6/1971 | Padberg |
| 3,785,382 A | 1/1974 | Schmidt-Kloiber et al. |
| 3,902,499 A | 9/1975 | Shene |
| 3,942,531 A | 3/1976 | Hoff et al. |
| 4,027,674 A | 6/1977 | Tessler et al. |
| 4,030,505 A | 6/1977 | Tessler |
| 4,445,509 A | 5/1984 | Auth |
| 4,662,126 A | 5/1987 | Malcolm |
| 4,662,375 A | 5/1987 | Hepp et al. |
| 4,671,254 A | 6/1987 | Fair |
| 4,685,458 A | 8/1987 | Leckrone |
| 4,741,405 A | 5/1988 | Moeny et al. |
| 4,809,682 A | 3/1989 | Forssmann et al. |
| 4,813,934 A | 3/1989 | Engelson et al. |
| 4,870,953 A | 10/1989 | DonMicheal et al. |
| 4,878,495 A | 11/1989 | Grayzel |
| 4,890,603 A | 1/1990 | Filler |
| 4,900,303 A | 2/1990 | Lemelson |
| 4,990,134 A | 2/1991 | Auth |
| 4,994,032 A | 2/1991 | Sugiyama et al. |
| 5,009,232 A | 4/1991 | Hassler et al. |
| 5,046,503 A | 9/1991 | Schneiderman |
| 5,057,103 A | 10/1991 | Davis |
| 5,057,106 A | 10/1991 | Kasevich et al. |
| 5,061,240 A | 10/1991 | Cherian |
| 5,078,717 A | 1/1992 | Parins et al. |
| 5,102,402 A | 4/1992 | Dror et al. |
| 5,103,556 A | 4/1992 | Filip et al. |
| 5,103,804 A | 4/1992 | Abele et al. |
| 5,116,227 A | 5/1992 | Levy |
| 5,125,928 A | 6/1992 | Parins et al. |
| 5,150,717 A | 9/1992 | Rosen et al. |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,245,988 A | 9/1993 | Einars et al. |
| 5,246,447 A | 9/1993 | Rosen et al. |
| 5,254,121 A | 10/1993 | Manevitz et al. |
| 5,281,231 A | 1/1994 | Rosen et al. |
| 5,295,958 A | 3/1994 | Shturman |
| 5,304,134 A | 4/1994 | Kraus et al. |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,454,809 A | 10/1995 | Janssen |
| 5,472,406 A | 12/1995 | de la Torre et al. |
| 5,582,578 A | 12/1996 | Zhong et al. |
| 5,584,843 A | 12/1996 | Wulfman et al. |
| 5,603,731 A | 2/1997 | Whitney |
| 5,609,606 A | 3/1997 | O'Boyle |
| 5,662,590 A | 9/1997 | de la Torre et al. |
| 5,697,281 A | 12/1997 | Eggers et al. |
| 5,709,676 A | 1/1998 | Alt |
| 5,735,811 A | 4/1998 | Brisken |
| 5,846,218 A | 12/1998 | Brisken et al. |
| 5,891,089 A | 4/1999 | Katz et al. |
| 5,893,840 A | 4/1999 | Hull et al. |
| 5,931,805 A | 8/1999 | Brisken |
| 6,007,530 A | 12/1999 | Dornhofer et al. |
| 6,033,371 A | 3/2000 | Torre et al. |
| 6,056,722 A | 5/2000 | Jayaraman |
| 6,080,119 A | 6/2000 | Schwarze et al. |
| 6,083,232 A | 7/2000 | Cox |
| 6,090,104 A | 7/2000 | Webster et al. |
| 6,096,000 A | 8/2000 | Tachibana et al. |
| 6,113,560 A | 9/2000 | Simnacher |
| 6,132,444 A | 10/2000 | Shturman et al. |
| 6,146,358 A | 11/2000 | Rowe |
| 6,186,963 B1 | 2/2001 | Schwarze et al. |
| 6,210,404 B1 | 4/2001 | Shadduck |
| 6,210,408 B1 | 4/2001 | Chandrasekaran et al. |
| 6,215,734 B1 | 4/2001 | Moeny et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,364,894 B1 | 4/2002 | Healy et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | De La Torre et al. |
| 6,440,124 B1 | 8/2002 | Esch et al. |
| 6,494,890 B1 | 12/2002 | Shturman et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,666,834 B2 | 12/2003 | Restle et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 | 6/2004 | Fry |
| 6,855,123 B2 | 2/2005 | Nita |
| 6,939,320 B2 | 9/2005 | Lennox |
| 6,989,009 B2 | 1/2006 | Lafontaine |
| 7,066,904 B2 | 6/2006 | Rosenthal et al. |
| 7,087,061 B2 | 8/2006 | Chernenko et al. |
| 7,241,295 B2 | 7/2007 | Maguire |
| 7,309,324 B2 | 12/2007 | Hayes et al. |
| 7,389,148 B1 | 6/2008 | Morgan |
| 7,505,812 B1 | 3/2009 | Eggers et al. |
| 7,569,032 B2 | 8/2009 | Naimark et al. |
| 7,850,685 B2 | 12/2010 | Kunis et al. |
| 7,853,332 B2 | 12/2010 | Olsen et al. |
| 7,873,404 B1 | 1/2011 | Patton |
| 7,951,111 B2 | 5/2011 | Drasler et al. |
| 8,162,859 B2 | 4/2012 | Schultheiss et al. |
| 8,177,801 B2 | 5/2012 | Kallok et al. |
| 8,353,923 B2 | 1/2013 | Shturman |
| 8,556,813 B2 | 10/2013 | Cioanta et al. |
| 8,574,247 B2 | 11/2013 | Adams et al. |
| 8,709,075 B2 | 4/2014 | Adams et al. |
| 8,728,091 B2 | 5/2014 | Hakala et al. |
| 8,747,416 B2 | 6/2014 | Hakala et al. |
| 8,856,371 B2 | 10/2014 | Kariti et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Adams et al. |
| 9,138,249 B2 | 9/2015 | Adams et al. |

(56) References Cited

U.S. PATENT DOCUMENTS

| | | |
|---|---|---|
| 9,198,825 B2 | 12/2015 | Katragadda et al. |
| 9,333,000 B2 | 5/2016 | Hakala et al. |
| 9,421,025 B2 | 8/2016 | Hawkins et al. |
| 9,433,428 B2 | 9/2016 | Hakala et al. |
| 9,522,012 B2 | 12/2016 | Adams |
| 9,642,673 B2 | 5/2017 | Adams et al. |
| 9,730,715 B2 | 8/2017 | Adams |
| 9,993,292 B2 | 6/2018 | Adams et al. |
| 9,999,788 B2 | 6/2018 | Gattiker et al. |
| 10,039,561 B2 | 8/2018 | Adams et al. |
| 10,118,015 B2 | 11/2018 | De La Rama et al. |
| 10,149,690 B2 | 12/2018 | Hawkins et al. |
| 10,154,799 B2 | 12/2018 | Van Der Weide et al. |
| 10,159,505 B2 | 12/2018 | Hakala et al. |
| 10,206,698 B2 | 2/2019 | Hakala et al. |
| 10,226,265 B2 | 3/2019 | Ku et al. |
| 10,517,620 B2 | 12/2019 | Adams |
| 10,517,621 B1 | 12/2019 | Adams |
| 10,555,744 B2 | 2/2020 | Nguyen et al. |
| 10,682,178 B2 | 6/2020 | Adams et al. |
| 10,702,293 B2 | 7/2020 | Adams et al. |
| 10,709,462 B2 | 7/2020 | Nguyen et al. |
| 10,765,440 B2 | 9/2020 | Tozzi |
| 10,959,743 B2 | 3/2021 | Adams et al. |
| 10,973,538 B2 | 4/2021 | Hakala et al. |
| 11,000,299 B2 | 5/2021 | Hawkins et al. |
| 11,076,874 B2 | 8/2021 | Hakala et al. |
| 11,337,713 B2 | 5/2022 | Nguyen et al. |
| 11,432,834 B2 | 9/2022 | Adams |
| 11,478,261 B2 * | 10/2022 | Nguyen .............. A61B 17/22 |
| 11,534,187 B2 | 12/2022 | Bonutti |
| 11,596,423 B2 | 3/2023 | Nguyen et al. |
| 11,596,424 B2 | 3/2023 | Hakala et al. |
| 11,622,780 B2 | 4/2023 | Nguyen et al. |
| 11,696,799 B2 | 7/2023 | Adams et al. |
| 11,992,232 B2 | 5/2024 | Nguyen |
| 12,114,874 B2 | 10/2024 | Nguyen et al. |
| 2001/0044596 A1 | 11/2001 | Jaafar |
| 2002/0045890 A1 | 4/2002 | Celliers et al. |
| 2002/0077643 A1 | 6/2002 | Rabiner et al. |
| 2002/0082553 A1 | 6/2002 | Duchamp |
| 2002/0177889 A1 | 11/2002 | Brisken et al. |
| 2003/0004434 A1 | 1/2003 | Greco et al. |
| 2003/0088262 A1 | 5/2003 | Bonnette et al. |
| 2003/0176873 A1 * | 9/2003 | Chernenko ...... A61B 17/22022 606/127 |
| 2003/0229370 A1 | 12/2003 | Miller |
| 2004/0006333 A1 | 1/2004 | Arnold et al. |
| 2004/0010249 A1 | 1/2004 | Truckai et al. |
| 2004/0044308 A1 | 3/2004 | Naimark et al. |
| 2004/0097963 A1 | 5/2004 | Seddon |
| 2004/0097996 A1 | 5/2004 | Rabiner et al. |
| 2004/0158150 A1 | 8/2004 | Rabiner et al. |
| 2004/0162508 A1 | 8/2004 | Uebelacker |
| 2004/0193046 A1 | 9/2004 | Nash et al. |
| 2004/0249401 A1 | 12/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0075662 A1 | 4/2005 | Pedersen et al. |
| 2005/0090888 A1 | 4/2005 | Hines et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0228372 A1 | 10/2005 | Truckai et al. |
| 2005/0245866 A1 | 11/2005 | Azizi |
| 2005/0251131 A1 | 11/2005 | Lesh |
| 2006/0004286 A1 | 1/2006 | Chang et al. |
| 2006/0069424 A1 | 3/2006 | Acosta et al. |
| 2006/0074484 A1 | 4/2006 | Huber |
| 2006/0085054 A1 | 4/2006 | Zikorus et al. |
| 2006/0184076 A1 | 8/2006 | Gill et al. |
| 2006/0190022 A1 | 8/2006 | Beyar et al. |
| 2006/0221528 A1 | 10/2006 | Li et al. |
| 2007/0016112 A1 | 1/2007 | Schultheiss et al. |
| 2007/0088380 A1 | 4/2007 | Hirszowicz et al. |
| 2007/0129667 A1 | 6/2007 | Tiedtke et al. |
| 2007/0149966 A1 | 6/2007 | Dahla et al. |
| 2007/0156129 A1 | 7/2007 | Kovalcheck |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0250052 A1 | 10/2007 | Wham |
| 2007/0255270 A1 | 11/2007 | Carney |
| 2007/0282301 A1 | 12/2007 | Segalescu et al. |
| 2007/0299481 A1 | 12/2007 | Syed et al. |
| 2008/0033423 A1 | 2/2008 | Peacock |
| 2008/0097251 A1 | 4/2008 | Babaev |
| 2008/0188913 A1 | 8/2008 | Stone et al. |
| 2009/0041833 A1 | 2/2009 | Bettinger et al. |
| 2009/0177085 A1 | 7/2009 | Maxwell et al. |
| 2009/0227992 A1 | 9/2009 | Nir et al. |
| 2009/0230822 A1 | 9/2009 | Kushculey et al. |
| 2009/0247945 A1 | 10/2009 | Levit et al. |
| 2009/0254114 A1 | 10/2009 | Hirszowicz et al. |
| 2009/0299447 A1 | 12/2009 | Jensen et al. |
| 2010/0016862 A1 | 1/2010 | Hawkins et al. |
| 2010/0036294 A1 | 2/2010 | Mantell et al. |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0179424 A1 | 7/2010 | Warnking et al. |
| 2010/0286709 A1 | 11/2010 | Diamant et al. |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0208185 A1 | 8/2011 | Diamant et al. |
| 2011/0257523 A1 | 10/2011 | Hastings et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0116289 A1 | 5/2012 | Hawkins et al. |
| 2012/0143177 A1 | 6/2012 | Avitall et al. |
| 2012/0157991 A1 | 6/2012 | Christian |
| 2012/0203255 A1 | 8/2012 | Hawkins et al. |
| 2012/0221013 A1 | 8/2012 | Hawkins et al. |
| 2012/0253358 A1 | 10/2012 | Golan et al. |
| 2013/0023802 A1 * | 1/2013 | McIntosh .............. A61M 25/10 601/2 |
| 2013/0030431 A1 | 1/2013 | Adams |
| 2013/0041355 A1 | 2/2013 | Heeren et al. |
| 2013/0116714 A1 | 5/2013 | Adams et al. |
| 2013/0123694 A1 | 5/2013 | Subramaniyan et al. |
| 2013/0150874 A1 | 6/2013 | Kassab |
| 2013/0158453 A1 | 6/2013 | Brouillette et al. |
| 2013/0253622 A1 | 9/2013 | Hooven |
| 2014/0039513 A1 * | 2/2014 | Hakala .............. A61B 17/2202 606/128 |
| 2014/0046229 A1 | 2/2014 | Hawkins et al. |
| 2014/0155830 A1 | 6/2014 | Bonnette et al. |
| 2014/0214061 A1 | 7/2014 | Adams et al. |
| 2015/0238209 A1 | 8/2015 | Hawkins et al. |
| 2015/0320432 A1 | 11/2015 | Adams |
| 2016/0151081 A1 | 6/2016 | Adams et al. |
| 2016/0184570 A1 | 6/2016 | Grace et al. |
| 2016/0262784 A1 * | 9/2016 | Grace .............. A61B 17/22022 |
| 2016/0324534 A1 | 11/2016 | Hawkins et al. |
| 2017/0135709 A1 | 5/2017 | Nguyen et al. |
| 2017/0231649 A1 * | 8/2017 | Rabiner ........... A61B 17/22004 606/128 |
| 2017/0311965 A1 | 11/2017 | Adams |
| 2018/0098779 A1 | 4/2018 | Betelia et al. |
| 2018/0360482 A1 | 12/2018 | Nguyen |
| 2019/0069916 A1 | 3/2019 | Hawkins et al. |
| 2020/0085458 A1 | 3/2020 | Nguyen et al. |
| 2021/0007760 A1 | 1/2021 | Reisin |
| 2021/0085383 A1 | 3/2021 | Vo et al. |
| 2021/0282792 A1 | 9/2021 | Adams et al. |
| 2021/0338258 A1 | 11/2021 | Hawkins et al. |
| 2022/0015785 A1 | 1/2022 | Hakala et al. |
| 2022/0125453 A1 | 4/2022 | Nguyen |

(56) References Cited

U.S. PATENT DOCUMENTS

| | | |
|---|---|---|
| 2022/0240958 A1 | 8/2022 | Nguyen et al. |
| 2023/0043475 A1 | 2/2023 | Adams |
| 2023/0181203 A1 | 6/2023 | Nguyen et al. |

FOREIGN PATENT DOCUMENTS

| | | |
|---|---|---|
| CA | 2104414 A1 | 2/1995 |
| CN | 1204242 A | 1/1999 |
| CN | 1269708 A | 10/2000 |
| CN | 1810211 A | 8/2006 |
| CN | 1942145 A | 4/2007 |
| CN | 101043914 A | 9/2007 |
| CN | 101534737 A | 9/2009 |
| CN | 102057422 A | 5/2011 |
| CN | 102271748 A | 12/2011 |
| CN | 102355856 A | 2/2012 |
| CN | 102765785 A | 11/2012 |
| CN | 203564304 U | 4/2014 |
| CN | 104582597 A | 4/2015 |
| CN | 107847259 A | 3/2018 |
| CN | 109843204 A | 6/2019 |
| DE | 3038445 A1 | 5/1982 |
| DE | 202006014285 U1 | 12/2006 |
| EP | 442199 A2 | 8/1991 |
| EP | 571306 A1 | 11/1993 |
| EP | 623360 A1 | 11/1994 |
| EP | 647435 A1 | 4/1995 |
| EP | 2253884 A1 | 11/2010 |
| EP | 2359764 A1 | 8/2011 |
| EP | 2362798 B1 | 4/2014 |
| JP | S58-032754 A | 2/1983 |
| JP | S60-191353 U | 12/1985 |
| JP | S62-099210 U | 6/1987 |
| JP | S62-275446 A | 11/1987 |
| JP | H03-63059 A | 3/1991 |
| JP | H06-125915 A | 5/1994 |
| JP | H07-47135 A | 2/1995 |
| JP | H08-89511 A | 4/1996 |
| JP | H10-99444 A | 4/1998 |
| JP | H10-314177 A | 12/1998 |
| JP | H10-513379 A | 12/1998 |
| JP | 2002538932 A | 11/2002 |
| JP | 2003500098 A | 1/2003 |
| JP | 2004081374 A | 3/2004 |
| JP | 2004357792 A | 12/2004 |
| JP | 2005501597 A | 1/2005 |
| JP | 2005095410 A | 4/2005 |
| JP | 2005515825 A | 6/2005 |
| JP | 2006516465 A | 7/2006 |
| JP | 2007289707 A | 11/2007 |
| JP | 2007532182 A | 11/2007 |
| JP | 2008506447 A | 3/2008 |
| JP | 2011513694 A | 4/2011 |
| JP | 2011520248 A | 7/2011 |
| JP | 2011524203 A | 9/2011 |
| JP | 2011528963 A | 12/2011 |
| JP | 2012505050 A | 3/2012 |
| JP | 2012508042 A | 4/2012 |
| JP | 2015522344 A | 8/2015 |
| JP | 2015525657 A | 9/2015 |
| JP | 2015528327 A | 9/2015 |
| JP | 2016508851 A | 3/2016 |
| JP | 6029828 B2 | 11/2016 |
| JP | 6081510 B2 | 2/2017 |
| JP | 2017035491 A | 2/2017 |
| WO | WO-1989011307 A1 | 11/1989 |
| WO | WO-1992003975 A1 | 3/1992 |
| WO | WO-1996024297 A1 | 8/1996 |
| WO | WO-1999000060 A1 | 1/1999 |
| WO | WO-1999002096 A1 | 1/1999 |
| WO | WO-2000051502 A1 | 9/2000 |
| WO | WO-2000056237 A2 | 9/2000 |
| WO | WO-2004069072 A2 | 8/2004 |
| WO | WO-2005034793 A2 | 4/2005 |
| WO | WO-2005099594 A1 | 10/2005 |
| WO | WO-2005102199 A1 | 11/2005 |
| WO | WO-2006006169 A2 | 1/2006 |
| WO | WO-2006127158 A2 | 11/2006 |
| WO | WO-2007088546 A2 | 8/2007 |
| WO | WO-2007149905 A2 | 12/2007 |
| WO | WO-2009121017 A1 | 10/2009 |
| WO | WO-2009126544 A1 | 10/2009 |
| WO | WO-2009136268 A2 | 11/2009 |
| WO | WO-2009152352 A2 | 12/2009 |
| WO | WO-2010014515 A2 | 2/2010 |
| WO | WO-2010014515 A3 | 8/2010 |
| WO | WO-2010054048 A3 | 9/2010 |
| WO | WO-2011006017 A1 | 1/2011 |
| WO | WO-2011094111 A2 | 8/2011 |
| WO | WO-2011143468 A2 | 11/2011 |
| WO | WO-2012025833 A2 | 3/2012 |
| WO | WO-2013059735 A1 | 4/2013 |
| WO | WO-2014025397 A1 | 2/2014 |
| WO | WO-2014025620 A1 | 2/2014 |
| WO | WO-2015017499 A1 | 2/2015 |
| WO | WO-2016109739 A1 | 7/2016 |
| WO | WO-2018067656 A1 | 4/2018 |
| WO | WO-2019099218 A1 | 5/2019 |
| WO | WO-2019152898 A1 | 8/2019 |

OTHER PUBLICATIONS

Advisory Action received for U.S. Appl. No. 13/615,107, mailed on Nov. 6, 2015, 3 pages.
Advisory Action Received for U.S. Appl. No. 12/482,995, mailed on Jun. 2, 2014, 3 pages.
Advisory Action Received for U.S. Appl. No. 12/482,995, mailed on Sep. 29, 2011, 2 pages.
Advisory Action Received for U.S. Appl. No. 12/581,295, mailed on Jul. 3, 2014, 3 pages.
Advisory Action Received for U.S. Appl. No. 13/049,199, mailed on Jun. 7, 2012, 3 pages.
Advisory Action received for U.S. Appl. No. 13/267,383, mailed on Jan. 6, 2014, 4 pages.
After Orbital Atherectomy Video (post treatment) Video 2019.
Amendment After Final Action received for U.S. Appl. No. 12/482,995, filed May 16, 2014, 8 pages.
Amendment in Response to Non-Final Office Action received for U.S. Appl. No. 12/482,995, filed Jan. 9, 2014 Jan. 9, 2014, 9 pages.
Amighi et al., (2005). "Impact of the Rapid-Exchange Versus Over-the-Wire Technique on Procedural Complications of Renal Artery Angioplasty," J Endovasc Ther., 12:233-239.
Armstrong, Ehrin Responses to Question 6 by Patent Owner's Declarants Ehrin Armstrong, Jan. 29, 2020, 5 pages.
Armstrong, Ehrin Responses to Questions 1-5 by Patent Owner's Declarants Ehrin Armstrong, Jan. 24, 2020, 4 pages.
Athanasoulis, (1980). "Percutaneous Transluminal Angioplasty: General Principles," American journal of Roentgenology, 135:893-900.
Bank of America Merrill Lynch A Simple Solution to a Difficult (and Large) Problem—Initiating Coverage of SWAV Shockwave Medical Inc., Apr. 1, 2019, pp. 1-22.
Becker et al., (1988). "Radiofrequency Balloon Angioplasty," Rationale and Proof of Principle Investigative Radiology, 23(11):810-817.
Before Orbital Aterectomy Video (pre-treatment) Video 2019.
Ben-Dor et al., "Handbook of Shock Waves", Shockwave Medical, Inc. Patent Owner Exhibit 2223, vol. 2, 2001, 824 pages.
Bittl et al., (1993). "Coronary Artery Perforation during Excimer Laser Coronary Angioplasty," Journal of the American College of Cardiology, 21(5):1158-1165.
Bittl et al., (1993). "Publication Information—Coronary Artery Perforation during Excimer Laser Coronary Angioplasty," Journal of the American College of Cardiology, 21(5): 1-6.
Bom et al., (1988). "Intra-Arterial Ultrasonic Imaging for Recanalization by Spark Erosion," Ultrasound in Medicine & Biology, 14(4):257-261.
Brinton et al., (2016). "Publication Information—TCT-777 Safety and Performance of the Shockwave Medical Lithoplasty® System in Treating Calcified Peripheral Vascular Lesions: 6-Month Results

(56) References Cited

OTHER PUBLICATIONS from the Two-Phase Disrupt PAD Study," Journal of the American College of Cardiology, 68(18):1-5.

Brinton et al., (2016). "TCT-777 Safety and Performance of the Shockwave Medical Lithoplasty® System in Treating Calcified Peripheral Vascular Lesions: 6-Month Results from the Two-Phase Disrupt PAD Study," Journal of the American College of Cardiology, 68(18):B314.

Brodmann et al., (2018). "Primary outcomes and mechanism of action of intravascular lithotripsy in calcified femoropopliteal lesions: Results of the Disrupt PAD II," Catheter Cardiovasc Interv., 93(2):335-342.

Calcium in the Peripheral and Coronary Arteries: The Pathologist View, Deposition Exhibit from Deposition of Dr. Finn, Mar. 6, 2020, 27 pages.

Canfield et al., (2018). "40 Years of Percutaneous Coronary Intervention: History and Future Directions," Journal of Personalized Medicine, 8(33):1-9.

Cardiology Today's Intervention Shockwave Attracts Additional Investment from Abiomed, has IPO Available Online at <https://www.healio.com/cardiac-vascular-intervention/peripheral/news/online/%7Bf96c1e20-b4a9-4167-bdb8-254e86a8182a%7D/shockwave-attracts-additional-investment-from-abiomed-has-ipo> Mar. 12, 2019, pp. 1-2.

Chart of Mantell Detailed Mapping of Provisional to '371 Claims Case No. IPR2019-00405 2020, 12 pages.

Cleveland et al., (2012). "Chapter 38: The Physics of Shock Wave Lithotripsy," Extracorporeal Shock Wave Lithotripsy, 4:317-332.

Concise Description of Relevance Accompanying Third Party Preissuance Submission Under 37 CFR 1.290 for U.S. Appl. No. 15/817,073, filed Aug. 5, 2019, 31 pages.

Connors et al., (2003). "Renal Nerves Mediate Changes in Contralateral Renal Blood Flow after Extracorporeal Shockwave Lithotripsy," Nephron Physiol, 95:67-75.

Das et al., (2014). "Technique Optimization of Orbital Atherectomy in Calcified Peripheral Lesions of the Lower Extremities," Catheterization and Cardiov Interv, 83:115-122.

Deagon, Brian Technology—Shockwave Medical IPO Soars on First Day of Trading Investor's Business Daily, Available Online at <https://www.investors.com/news/technology/shockwave-medical-ipo-soars-trading/> Mar. 7, 2019, pp. 1-15.

Decision Instituting Inter Partes Review for U.S. Pat. No. 8,956,371, by the Patent Trial and Appeal Board dated Jul. 9, 2019, 28 pages.

Decision of Appeals Notice received for Japanese Patent Application No. 2011-534914, mailed on Oct. 17, 2016, 4 pages.

Decision to Grant received for European Patent Application No. 13756766.5, mailed on May 27, 2016, 2 pages.

Decision to Grant received for European Patent Application No. 09763640.1, mailed on Feb. 22, 2018, 2 pages.

Decision to Grant received for European Patent Application No. 09825393.3, mailed on Mar. 13, 2014, 2 pages.

Decision to Grant received for Japanese Patent Application No. 2011-513694, mailed on Oct. 7, 2014, 3 pages (Official Copy Only) (See Communication under 37 CFR § 1.98(a) (3)).

Declaration and CV of *Aloke V. Finn* Case IPR2019-00405 Feb. 20, 2020, 45 pages.

Declaration and CV of Jeffrey Chambers Case IPR2019-00405 Dec. 19, 2020, 32 pages.

Declaration of Dr. Morten Olgaard Jensen dated Dec. 6, 2018, pp. 1-137.

Declaration of Juanita DeLoach Exhibit 1236, Case IPR2019-00408 Feb. 18, 2020, 4 pages.

Declaration of Natalie J. Grace dated Apr. 10, 2019, pp. 1-3.

Deposition Exhibit from Deposition of Dr. Jensen, Balloon Attributes that Impact Deliverability, Mar. 4, 2020, 1 page.

Deposition Exhibit from Deposition of Dr. Jensen, Diagram from Wikipedia Page for Balloon Catheters, Mar. 4, 2020, 1 page.

Deposition Exhibit from Deposition of Dr. Jensen, Figures 1 and 2 of JP Patent No. 62-275446 (color added), Mar. 4, 2020, 1 page.

Deposition Exhibit from Deposition of Dr. Jensen, Handwritten Diagram, Mar. 4, 2020, 1 page.

Deposition Exhibit of Ronald David Berger Case No. IPR2019-00405 Jan. 27, 2020, 42 pages.

Deposition Transcript (compressed) of Dr. Aloke Finn, Case No. IPR2019-00405, Mar. 6, 2020, 31 pages.

Deposition Transcript (compressed) of Dr. Daniel van der Weide, Case No. IPR2019-00409, U.S. Pat. No. 8,728,091 B2, Jan. 10, 2020., 111 pages.

Deposition Transcript (compressed) of Dr. Jeffrey Chambers, Case No. IPR2019-00405, Mar. 2, 2020., 81 pages.

Deposition Transcript (compressed) of Dr. Morten Olgaard Jensen, Case No. IPR2019-00405, U.S. Pat. No. 8,956,371, Mar. 4, 2020, 73 pages.

Deposition Transcript (compressed) of Dr. Morten Olgaard Jensen, Case No. IPR2019-00408, U.S. Pat. No. 9,642,673, Feb. 26, 2020., 80 pages.

Deposition Transcript (compressed) of Ronald David Berger Case No. IPR2019-00405 Jan. 27, 2020, 103 pages.

Dewhirst et al., (2003). "Basic Principles of Thermal Dosimetry and Thermal Thresholds for Tissue Damage from Hyperthermia International," Journal of Hyperthermia, 19(3):267-294.

Dewhirst et al., (2003). "Publication Information—Basic Principles of Thermal Dosimetry and Thermal Thresholds for Tissue Damage from Hyperthermia," International Journal of Hyperthermia, 19(3):1-3.

Diamondback 360® Peripheral Orbital Atherectomy System, Cardiovascular Systems, Inc., Patent Owner Exhibit 2231, 2019, 58 pages.

Dictionary.com Definition of 'Angioplasty' Available Online at <https://www.dictionary.com/browse/angioplasty> pp. 1-5.

Dodd, (1842). "Two Cases of Calculus in the Bladder, in Which Lithotripsy Was Performed," Provincial Medical & Surgical Journal, 3(71):368-370.

Dodge Jr., et al., (1992). "Lumen Diameter of Normal Human Coronary Arteries," Influence of Age, Sex, Anatomic Variation, and Left Ventricular Hypertrophy or Dilation Circulation, 86(1):232-246.

E-mail from Cook Alciati to Mark Nelson confirming Dr. Chamber's total compensation amount from Cardiovascular Systems, Inc, *CSI* v. *Shockwave*—Dr. Chambers Testimony, Mar. 20, 2020, 1 page.

Extended European Search Report (includes Supplementary European Search Report and Search Opinion) received for European Patent Application No. 09763640.1, mailed on Oct. 10, 2013, 5 pages.

Extended European Search Report and Search Opinion received for European Patent Application No. 09825393.3, mailed on Feb. 28, 2013, 6 pages.

Extended European Search Report received for European Patent Application No. 13827971.6, mailed on Apr. 12, 2016, 8 pages.

Farb et al., (2002). "Morphological Predictors of Restenosis After Coronary Stenting in Humans," Circulation, pp. 2974-2980.

FDA Clears Lithoplasty Balloon That Shatters Calcified Lesions With Ultrasound Diagnostic and Interventional Cardiology, Available Online at <https://www.dicardiology.com/product/fda-clearslithoplasty-balloon-shatters-calcified-lesions-ultrasound> Sep. 16, 2016, pp. 1-5.

Fernandes et al., (2007). "Enhanced infarct border zone function and altered mechanical activation predict inducibility of monomorphic ventricular tachycardia in patients with ischemic cardiomyopathy," Radiology, 245(3):712-719.

File History of U.S. Pat. No. 8,956,371, pp. 1-1561.

Final Office Action received for U.S. Appl. No. 12/482,995, mailed on Jul. 22, 2011, 14 pages.

Final Office Action received for U.S. Appl. No. 12/501,619, mailed on Feb. 21, 2012, 12 pages.

Final Office Action received for U.S. Appl. No. 12/611,997, mailed on Dec. 11, 2012, 9 pages.

Final Office Action received for U.S. Appl. No. 12/611,997, mailed on Nov. 10, 2011, 15 pages.

Final Office Action received for U.S. Appl. No. 13/049,199, mailed on Apr. 4, 2012, 10 pages.

(56) References Cited

OTHER PUBLICATIONS

Final Office Action received for U.S. Appl. No. 13/207,381, mailed on Nov. 2, 2012, 7 pages.
Final Office Action received for U.S. Appl. No. 14/271,342 mailed on Feb. 27, 2015, 7 pages.
Final Office Action received for U.S. Appl. No. 12/482,995, mailed on Feb. 20, 2014, 11 pages.
Final Office Action received for U.S. Appl. No. 12/581,295, mailed on Jun. 5, 2014, 14 pages.
Final Office Action received for U.S. Appl. No. 12/611,997, mailed on Oct. 24, 2013, 10 pages.
Final Office Action received for U.S. Appl. No. 13/049,199 mailed on Aug. 11, 2014, 8 pages.
Final Office Action received for U.S. Appl. No. 13/207,381, mailed on Nov. 7, 2013, 7 pages.
Final Office Action Received for U.S. Appl. No. 13/267,383, mailed on May 28, 2015, 12 pages.
Final Office Action received for U.S. Appl. No. 13/267,383, mailed on Oct. 25, 2013, 8 pages.
Final Office Action received for U.S. Appl. No. 13/534,658, mailed on Aug. 23, 2016, 11 pages.
Final Office Action received for U.S. Appl. No. 13/615,107 mailed on Sep. 1, 2015, 9 pages.
Final Office Action received for U.S. Appl. No. 13/646,570, mailed on Dec. 23, 2014, 10 pages.
Final Office Action received for U.S. Appl. No. 14/229,735, mailed on Aug. 27, 2015, 7 pages.
Final Office Action received for U.S. Appl. No. 14/273,063, mailed on Dec. 28, 2016, 11 pages.
Final Office Action received for U.S. Appl. No. 15/213,105, mailed on May 4, 2018, 8 pages.
Final Office Action received for U.S. Appl. No. 14/660,539, mailed on Aug. 3, 2017, 11 pages.
Final Written Decision *Ariosa Diagnostics Inc.* vs. *Illumina Inc.* dated Jan. 7, 2016, pp. 1-18.
Final Written Decision for U.S. Pat. No. 8,956,371, by the Patent Trial and Appeal Board dated Jul. 8, 2020, 89 pages.
Fung, Y. C. Biomechanics—Mechanical Properties of Living Tissues Second Edition, Springer 1993, 14 pages.
Gambihler et al., (1994). "Permeabilization of the Plasma Membrane of LI210 Mouse Leukemia Cells Using Lithotripter Shock Waves," The Journal of Membrane Biology, 141:267-275.
Gottlieb, Scott U.S. Department of Health and Human Services, Food and Drug Administration Report to Congress by Scott Gottlieb Exhibit 1217 Sep. 30, 2018, 10 pages.
Grassi et al., (2012). "Novel Antihypertensive Therapies: Renal Sympathetic Nerve Ablation and Carotid Baroreceptor Stimulation," Curr Hypertens Rep, 14:567-572.
Grocela et al., (1997). "Intracorporeal Lithotripsy," Instrumentation and Development Urologic Clinics of North America, 24(1):13-23.
Hawkins, et al. U.S. Appl. No. 61/061,170, filed on Jun. 13, 2008, titled "Shockwave Balloon Catheter System".
Hill, Jonathan M., Deposition Transcript (compressed) of Jonathan M. Hill, M.D. Exhibit 1211, Case No. IPR2019-00408, U.S. Pat. No. 9,642,673 Dec. 16, 2019, 63 pages.
Hodges et al., (1994). "Publication Information—Ultrasound Determination of Total Arterial Wall Thickness," Journal of Vascular Surgery, 19(4):1-13.
Hodges et al., (1994). "Ultrasound Determination of Total Arterial Wall Thickness," Journal of Vascular Surgery, 19(4):745-753.
Huang et al., (1998). "Cost Effectiveness of Electrohydraulic Lithotripsy v Candela Pulsed-Dye Laser in Management of the Distal Ureteral Stone," Journal of Endourology, 12(3):237-240.
Intention to Grant received for European Patent Application No. 09763640.1, mailed on Oct. 11, 2017, 8 pages.
Intention to Grant received for European Patent Application No. 13756766.5, mailed on Jan. 8, 2016, 5 pages.
Intention to Grant received for European Patent Application No. 13827971.6, mailed on Sep. 28, 2018, 8 pages.

International Preliminary Report on Patentability received for PCT Patent Application No. PCT/US2009/047070, mailed on Dec. 23, 2010, 7 pages.
International Preliminary Report on Patentability received for PCT Patent Application No. PCT/US2009/063354, mailed on May 19, 2011, 6 pages.
International Preliminary Report on Patentability received for PCT Patent Application No. PCT/US2011/047070, mailed on Feb. 21, 2013, 7 pages.
International Preliminary Report on Patentability received for PCT Patent Application No. PCT/US2012/023172, mailed on Aug. 15, 2013, 6 pages.
International Preliminary Report on Patentability received for PCT Patent Application No. PCT/US2012/063925, mailed on May 22, 2014, 12 pages.
International Preliminary Report on Patentability received for PCT Patent Application No. PCT/US2013/031805, mailed on Feb. 19, 2015, 11 pages.
International Preliminary Report on Patentability received for PCT Patent Application No. PCT/US2013/039987 issued on Nov. 20, 2014, 11 pages.
International Preliminary Report on Patentability received for PCT Patent Application No. PCT/US2013/048277 mailed on Jan. 8, 2015, 9 pages.
International Preliminary Report on Patentability received for PCT Patent Application No. PCT/US2013/055431, mailed on Feb. 26, 2015, 7 pages.
International Preliminary Report on Patentability received for PCT Patent Application No. PCT/US2013/059533 mailed on Mar. 26, 2015, 10 pages.
International Preliminary Report on Patentability received for PCT Patent Application No. PCT/US2015/029088, mailed on Nov. 17, 2016, 8 pages.
International Preliminary Report on Patentability received for PCT Patent Application No. PCT/US2016/060817, mailed on May 31, 2018, 9 pages.
International Preliminary Report on Patentability received for PCT Patent Application No. PCT/US2018/059083, mailed on May 28, 2020, 6 pages.
International Preliminary Report on Patentability received for PCT Patent Application No. PCT/US2019/035750, mailed on Decemer 30, 2020, 11 pages.
International Search Report and Written Opinion Received for PCT Application No. PCT/US2018/034855 , mailed on Aug. 23, 2018, 13 pages.
International Search Report and Written Opinion Received for PCT Application No. PCT/US2018/059083, mailed on Jan. 22, 2019, 8 pages.
International Search Report and Written Opinion received for PCT Patent Application No. PCT/US2013/031805 mailed on May 20, 2013, 13 pages.
International Search Report and Written Opinion received for PCT Patent Application No. PCT/US2013/039987, mailed on Sep. 23, 2013, 15 pages.
International Search Report and Written Opinion received for PCT Patent Application No. PCT/US2013/048277, mailed on Oct. 2, 2013, 14 pages.
International Search Report and Written Opinion received for PCT Patent Application No. PCT/US2013/055431, mailed on Nov. 12, 2013, 9 pages.
International Search Report and Written Opinion received for PCT Patent Application No. PCT/US2013/059533, mailed on Nov. 7, 2013, 14 pages.
International Search Report and Written Opinion received for PCT Patent Application No. PCT/US2015/029088 mailed on Jul. 16, 2015, 13 pages.
International Search Report and Written Opinion received for PCT Patent Application No. PCT/US2016/060817, mailed on Feb. 20, 2017, 13 pages.
International Search Report and Written Opinion received for PCT Patent Application No. PCT/US2019/035750, mailed on Aug. 1, 2019, 21 pages.

(56) References Cited

OTHER PUBLICATIONS

International Search Report and Written Opinion received for PCT Patent Application No. PCT/US2020/046134, mailed on Oct. 26, 2020, 18 pages.
International Search Report and Written Opinion received for PCT Patent Application No. PCT/US2020/051551, mailed on Jan. 11, 2021, 16 pages.
International Search Report received for PCT Patent Application No. PCT/US2009/047070, mailed on Jan. 19, 2010, 4 pages.
International Search Report received for PCT Patent Application No. PCT/US2009/063354, mailed on Jun. 11, 2010, 3 pages.
International Search Report received for PCT Patent Application No. PCT/US2012/023172, mailed on Sep. 28, 2012, 3 pages.
International Written Opinion received for PCT Patent Application No. PCT/US2009/047070, mailed on Jan. 19, 2010, 5 pages.
International Written Opinion received for PCT Patent Application No. PCT/US2009/063354, mailed on Jun. 11, 2010, 4 pages.
International Written Opinion received for PCT Patent Application No. PCT/US2011/047070, mailed on May 1, 2012, 5 pages.
International Written Opinion received for PCT Patent Application No. PCT/US2012/023172, mailed on Sep. 28, 2012, 4 pages.
Jahnke et al., (2008). "Retrospective Study of Rapid-Exchange Monorail Versus Over-the-Wire Technique for Femoropopliteal Angioplasty," Cardiovascular and Interventional Radiology, 31:854-859.
Johnston et al., (2004). "Publication Information—Non-Newtonian Blood Flow in Human Right Coronary Arteries: Steady State Simulations," Journal of Biomechanics, 37(5):1-2.
Johnston et al., (2006). "Non-Newtonian Blood Flow in Human Right Coronary Arteries: Transient Simulations," Journal of Biomechanics, 39(6):1-35.
Kaplan et al., (1993). "Healing after Arterial Dilatation with Radiofrequency Thermal and Nonthermal Balloon Angioplasty Systems," Journal of Investigative Surgery, 6:33-52.
Kereiakes, Dean J., Deposition Transcript (compressed) of Dean J. Kereiakes Exhibit 1213, Cases No. 2019-00405, 00408 and 00409 Jan. 7, 2020, 65 pages.
Knuttinen et al., (2014). "Unintended Thermal Injuries from Radiofrequency Ablation: Organ Protection with an Angioplasty Balloon Catheter in an Animal Model," Journal of Clinical Imaging Science, 4(1):1-6.
Kodama et al., (2002). "Shock wave-mediated molecular delivery into cells," Biochimica et Biophysica Acta, 1542:186-194.
Lauer et al., (1997). "Shock wave permeabilization as a new gene transfer method," Gene Therapy, 4:710-715.
Lee et al., (1991). "Structure-Dependent Dynamic Mechanical Behavior of Fibrous Caps From Human Atherosclerotic Plaques," Circulation, 83(5):1764-1770.
Lee et al., (2017). "Orbital atherectomy for treating de novo, severely calcified coronary lesions: 3-year results of the pivotal ORBIT II trial," Cardiovascular Revascularization Medicine, 18:261-264.
Lee et al., (2018). "Acute Procedural Outcomes of Orbital Atherectomy for the Treatment of Profunda Femoris Artery Disease: Subanalysis of the CONFIRM Registries," J Invasive Cardio, 330(5):177-181.
Linnemeier et al., (1993). "Radiation Exposure: Comparison of Rapid Exchange and Conventional Over-the-Wire Coronary Angioplasty Systems," Catheterization and Cardiovascular Diagnosis, 30:11-14.
Lipowski, et al. U.S. Appl. No. 61/051,262 pp. 1-36.
Liu et al., (2015). "Current Understanding of Coronary Artery Calcification," Journal of Geriatric Cardiology, 12:668-675.
Med Device Online Angioplasty Balloons Advanced Polymers Inc., Available Online at <https://www.meddeviceonline.com/doc/angioplasty-balloons-0001>, 1 page.
MedlinePlus Angioplasty U.S. National Library of Medicine, Available Online at <https://medlineplus.gov/angioplasty.html>, pp. 1-4.
Meraj et al., (2018). "Clinical outcomes of Atherectomy Prior to Percutaneous Coronary Intervention: A Comparison of Outcomes following Rotational Versus Orbital Atherectomy (COAP-PCI study)," Journal of Interventional Cardiology, 31:478-485.
Mills et al., (2019). "Cracking the Code on Calcium; Initiate with BUY, $39 Target Canaccord Genuity—Capital Markets," US Equity Research Apr. 1, 2019, pp. 1-63.
Mitomo, "Intravascular lithotripsy: A Novel Technology for Treating Calcified Coronary Stenoses Cardiovascular News," Online Available at <https://cardiovascularnews.com/intravascular-lithotripsy-anovel-technology-for-treating-calcified-coronary-stenoses> Apr. 18, 2018, pp. 1-4.
Mooney et al., (1990). "Monorail Piccolino Catheter: A New Rapid Exchange/Ultralow Profile Coronary Angioplasty System," Catheterization and Cardiovascular Diagnosis, 20:114-119.
Mori et al., "Coronary Artery Calcification and its Progression—What Does it Really Mean", American College of Cardiology Foundation, vol. 11, No. 1, 2018, 16 pages.
Myler et al., (1987). "Recurrence After Coronary Aangioplasty," Catheterization and Cardiovascular Diagnosis, 13:77-86.
Nichols et al., (2005). "McDonald's Blood Flow in Arteries: Theoretical," Experimental and Clinical Principles 5th Edition, pp. 1-9.
Nisonson et al., (1986). "Ambulatory Extracorporeal Shockwave Lithotripsy," Urology, 28(5):381-384.
Non Final Office Action received for U.S. Appl. No. 12/482,995, mailed on Aug. 13, 2014, 10 pages.
Non Final Office Action received for U.S. Appl. No. 12/482,995, mailed on Jul. 12, 2013, 11 pages.
Non Final Office Action received for U.S. Appl. No. 12/611,997, mailed on Nov. 26, 2014, 8 pages.
Non Final Office Action received for U.S. Appl. No. 13/207,381, mailed on Nov. 25, 2014, 5 pages.
Non Final Office Action received for U.S. Appl. No. 13/465,264, mailed on Oct. 29, 2014, 13 pages.
Non Final Office Action received for U.S. Appl. No. 13/646,570, mailed on Oct. 29, 2014, 10 pages.
Non Final Office Action received for U.S. Appl. No. 14/079,463, mailed on Mar. 4, 2014, 9 pages.
Non Final Office Action received for U.S. Appl. No. 12/482,995, mailed on Feb. 11, 2011, 27 pages.
Non Final Office Action received for U.S. Appl. No. 12/501,619, mailed on Nov. 3, 2011, 10 pages.
Non Final Office Action received for U.S. Appl. No. 12/611,997, mailed on Apr. 8, 2013, 9 pages.
Non Final Office Action received for U.S. Appl. No. 12/611,997, mailed on Aug. 24, 2012, 11 pages.
Non Final Office Action received for U.S. Appl. No. 12/611,997, mailed on Jun. 21, 2011, 13 pages.
Non Final Office Action received for U.S. Appl. No. 13/049,199, mailed on Dec. 12, 2011, 10 pages.
Non Final Office Action received for U.S. Appl. No. 13/207,381, mailed on Feb. 22, 2013, 7 pages.
Non Final Office Action received for U.S. Appl. No. 13/207,381, mailed on Jun. 12, 2012, 6 pages.
Non Final Office Action received for U.S. Appl. No. 13/534,658, mailed on Mar. 11, 2016, 12 pages.
Non Final Office Action received for U.S. Appl. No. 14/218,858, mailed on Mar. 30, 2016, 13 pages.
Non Final Office Action received for U.S. Appl. No. 14/515,130, mailed on Jan. 14, 2016, 16 pages.
Non-Final Office Action received for U.S. Appl. No. 12/501,619, mailed on Jan. 28, 2014, 10 pages.
Non-Final Office Action received for U.S. Appl. No. 12/581,295, mailed on Jan. 15, 2015, 14 pages.
Non-Final Office Action received for U.S. Appl. No. 12/581,295, mailed on Mar. 10, 2014, 11 pages.
Non-Final Office Action received for U.S. Appl. No. 12/611,997, mailed on Feb. 13, 2014, 9 pages.
Non-Final Office Action received for U.S. Appl. No. 13/049,199, mailed on Feb. 4, 2014, 8 pages.
Non-Final Office Action received for U.S. Appl. No. 13/207,381, mailed on Feb. 25, 2014, 8 pages.
Non-Final Office Action received for U.S. Appl. No. 13/267,383, mailed on Feb. 25, 2015, 9 pages.
Non-Final Office Action received for U.S. Appl. No. 13/465,264, mailed on Dec. 23, 2014, 13 pages.

(56) References Cited

OTHER PUBLICATIONS

Non-Final Office Action received for U.S. Appl. No. 13/615,107, mailed on Apr. 24, 2015, 9 pages.
Non-Final Office Action received for U.S. Appl. No. 13/646,583, mailed on Oct. 31, 2014, 8 pages.
Non-Final Office Action received for U.S. Appl. No. 14/061,554, mailed on Mar. 12, 2014, 14 pages.
Non-Final Office Action received for U.S. Appl. No. 14/271,276, mailed on Aug. 4, 2014, 7 pages.
Non-Final Office Action received for U.S. Appl. No. 14/271,342, mailed on Sep. 2, 2014, 6 pages.
Non-Final Office Action received for U.S. Appl. No. 14/273,063, mailed on Jun. 3, 2016, 9 pages.
Non-Final Office Action received for U.S. Appl. No. 14/660,539, mailed on Nov. 24, 2017, 10 pages.
Non-Final Office Action received for U.S. Appl. No. 14/693,155, mailed on Jan. 15, 2016, 6 pages.
Non-Final Office Action received for U.S. Appl. No. 15/213,105, mailed on Nov. 28, 2017, 7 pages.
Non-Final Office Action received for U.S. Appl. No. 15/346,132, mailed on Dec. 20, 2018, 14 pages.
Non-Final Office Action received for U.S. Appl. No. 15/474,885, mailed on Oct. 5, 2017, 9 pages.
Non-Final Office Action received for U.S. Appl. No. 15/652,070, mailed on Jan. 11, 2019, 9 pages.
Non-Final Office Action received for U.S. Appl. No. 15/817,073, mailed on Nov. 12, 2019, 18 pages.
Non-Final Office Action received for U.S. Appl. No. 14/660,539, mailed on Mar. 6, 2017, 14 pages.
Non-Final Office Action received for U.S. Appl. No. 16/436,186, mailed on Sep. 21, 2021, 16 pages.
Non-Final Office Action received for U.S. Appl. No. 17/025,866, mailed on Mar. 2, 2022, 9 pages.
Notice of Acceptance Received for Australian Patent Application No. 2009257368, mailed on Aug. 28, 2014, 2 pages.
Notice of Acceptance Received for Australian Patent Application No. 2009313507, mailed on Nov. 17, 2014, 2 pages.
Notice of Acceptance received for Australian Patent Application No. 2013284490, mailed on May 8, 2018, 3 pages.
Notice of Acceptance received for Australian Patent Application No. 2013300176, mailed on Aug. 7, 2017, 3 pages.
Notice Of Allowance received for Japanese Patent Application No. 2015-520522, mailed on Feb. 23, 2017. 3 pages of Official Copy Only.
Notice of Allowance received for Canadian Patent Application No. 2,727,429, mailed on May 26, 2015, 1 page.
Notice of Allowance received for Canadian Patent Application No. 2,779,600, mailed on Jul. 7, 2017, 1 page.
Notice of Allowance received for Chinese Patent Application No. 201380033808.3, mailed on Dec. 29, 2016, 4 pages (Official Copy Only).
Notice of Allowance received for Chinese Patent Application No. 201380041656.1, mailed on Mar. 3, 2017, 4 pages (Official Copy Only).
Notice of Allowance received for Japanese Patent Application No. 2015-036444, mailed on Jan. 13, 2017, 3 pages (Official Copy Only).
Notice of Allowance received for Japanese Patent Application No. 2015-520522, mailed on Feb. 23, 2017, 3 pages (Official Copy Only).
Notice of Allowance received for Japanese Patent Application No. 2015-526523, mailed on Dec. 4, 2017, 3 pages (Official Copy Only) (See Communication under 37 CFR § 1.98(a) (3)).
Notice of Allowance received for Japanese Patent Application No. 2016-143049, mailed on Nov. 13, 2017, 3 pages (Official copy only).
Notice of Allowance received for Japanese Patent Application No. 2017-212658, mailed on May 13, 2019, 3 pages (Official Copy Only).
Notice of Allowance received for U.S. Appl. No. 15/652,070, mailed on May 21, 2019, 8 pages.
Notice of Allowance received for U.S. Appl. No. 14/515,130, mailed on May 2, 2016, 8 pages.
Notice of Allowance received for U.S. Appl. No. 14/515,130, mailed on May 25, 2016, 3 pages.
Notice of Allowance received for U.S. Appl. No. 12/581,295, mailed on Jul. 10, 2015, 15 pages.
Notice of Allowance received for U.S. Appl. No. 12/581,295, mailed on Jul. 29, 2015, 7 pages.
Notice of Allowance received for U.S. Appl. No. 12/611,997, mailed on Apr. 15, 2015, 7 pages.
Notice of Allowance received for U.S. Appl. No. 13/207,381, mailed on Apr. 14, 2015, 7 pages.
Notice of Allowance received for U.S. Appl. No. 13/465,264, mailed on May 8, 2015, 7 pages.
Notice of Allowance received for U.S. Appl. No. 13/957,276, mailed on Aug. 28, 2015, 9 pages.
Notice of Allowance received for U.S. Appl. No. 14/271,276, mailed on Feb. 25, 2015, 8 pages.
Notice of Allowance received for U.S. Appl. No. 12/482,995, mailed on Dec. 24, 2014, 6 pages.
Notice of Allowance received for U.S. Appl. No. 13/049,199, mailed on Dec. 15, 2014, 7 pages.
Notice of Allowance received for U.S. Appl. No. 13/049,199, mailed on Jan. 13, 2015, 4 pages.
Notice of Allowance received for U.S. Appl. No. 13/534,658, mailed on Jan. 5, 2017, 6 pages.
Notice of Allowance received for U.S. Appl. No. 13/534,658, mailed on Jan. 18, 2017, 4 pages.
Notice of Allowance received for U.S. Appl. No. 13/646,570, mailed on Mar. 11, 2015, 7 pages.
Notice of Allowance received for U.S. Appl. No. 13/777,807, mailed on May 19, 2015, 13 pages.
Notice of Allowance received for U.S. Appl. No. 13/831,543, mailed on Oct. 8, 2014, 14 pages.
Notice of Allowance received for U.S. Appl. No. 14/061,554, mailed on Apr. 25, 2014, 8 pages.
Notice of Allowance received for U.S. Appl. No. 14/079,463, mailed on Apr. 1, 2014, 5 pages.
Notice of Allowance received for U.S. Appl. No. 14/218,858, mailed on Aug. 26, 2016, 8 pages.
Notice of Allowance received for U.S. Appl. No. 14/271,342, mailed on Mar. 13, 2015, 5 pages.
Notice of Allowance received for U.S. Appl. No. 14/273,063, mailed on Apr. 12, 2017. 7 pages.
Notice of Allowance received for U.S. Appl. No. 14/660,539, mailed on Apr. 6, 2018, 7 pages.
Notice of Allowance received for U.S. Appl. No. 14/693,155, mailed on Apr. 26, 2016, 9 pages.
Notice of Allowance received for U.S. Appl. No. 15/213,105, mailed on Aug. 10, 2018, 8 pages.
Notice of Allowance received for U.S. Appl. No. 15/220,999, mailed on Oct. 10, 2018, 10 pages.
Notice of Allowance received for U.S. Appl. No. 15/474,885, mailed on Feb. 14, 2018, 5 pages.
Notice of Allowance received for U.S. Appl. No. 15/817,073, mailed on Mar. 13, 2020, 8 pages.
Notice of Allowance received for U.S. Appl. No. 13/615,107, mailed on Dec. 31, 2015, 10 pages.
Notice of Allowance received for U.S. Appl. No. 17/025,866, mailed on Jun. 23, 2022, 8 pages.
Office Action received for Japanese Patent Application No. 2016-143049, mailed on Jul. 28, 2017, 7 pages (4 pages of English Translation and 3 pages of Official copy).
Office Action received for Australian Patent Application No. 2009257368, issued on Apr. 28, 2014, 4 pages.
Office Action received for Australian Patent Application No. 2009257368, issued on Jul. 31, 2013, 4 pages.
Office Action received for Australian Patent Application No. 2009313507, mailed on Nov. 13, 2013, 3 pages.
Office Action received for Australian Patent Application No. 2013284490, mailed on Jun. 5, 2017, 4 pages.

(56) References Cited

OTHER PUBLICATIONS

Office Action received for Australian Patent Application No. 2013284490, mailed on May 3, 2018, 5 pages.
Office Action received for Australian Patent Application No. 2013300176, mailed on Nov. 10, 2016, 2 pages.
Office Action received for Australian Patent Application No. 2018204691, mailed on Jul. 12, 2018, 2 pages.
Office Action received for Canadian Patent Application No. 2,727,429, mailed on Apr. 14, 2015, 4 pages.
Office Action received for Canadian Patent Application No. 2,779,600, mailed on Jan. 4, 2016, 6 pages.
Office Action received for Canadian Patent Application No. 2,779,600, mailed on Oct. 19, 2016, 3 pages.
Office Action received for Chinese Patent Application No. 200980153687.X, mailed on Dec. 26, 2012, 11 pages of Official copy only.
Office Action received for Chinese Patent Application No. 200980153687.X, mailed on Jul. 11, 2013, 11 pages (Official copy only).
Office Action received for Chinese Patent Application No. 201380033808.3, mailed on Jul. 5, 2016, 9 pages (3 pages of English translation and 6 pages of Official copy).
Office Action received for Chinese Patent Application No. 201380041656.1, mailed on Jul. 5, 2016, 9 pages (4 pages of English translation and 5 pages of Official copy).
Office Action received for Chinese Patent Application No. 201380042887.4, mailed on Aug. 8, 2016, 9 pages (4 pages of English translation and 5 pages of Official copy).
Office Action received for European Patent Application No. 13735174.8, mailed on Oct. 15, 2018, 5 pages.
Office Action received for European Patent Application No. 09763640.1, mailed on Dec. 2, 2016, 4 pages.
Office Action received for Japanese Patent Application No. 2011-513694, mailed on Aug. 27, 2013, 6 pages (3 pages of English Translation and 3 pages of Official copy).
Office Action Received for Japanese Patent Application No. 2011-513694, mailed on Jun. 10, 2014, 4 pages total (2 pages of Official Copy and 2 pages of English Translation).
Office Action Received for Japanese Patent Application No. 2011-534914, mailed on Jan. 13, 2015, 9 pages (7 pages of English Translation and 2 pages of Official Copy.
Office Action Received for Japanese Patent Application No. 2011-534914, mailed on Jul. 15, 2014, 3 pages (1 page of English Translation and 2 pages of Official Copy).
Office Action received for Japanese Patent Application No. 2011-534914, mailed on May 10, 2016, 10 pages ( 4 pages of Official Copy and 6 pages of English Translation).
Office Action received for Japanese Patent Application No. 2011-534914, mailed on Oct. 1, 2013, 5 pages (2 pages of English Translation and 3 pages of Official copy).
Office Action received for Japanese Patent Application No. 2014-158517, mailed on Feb. 15, 2017, 8 pages (5 pages of English Translation and 3 pages of Official Copy Only).
Office Action Received for Japanese Patent Application No. 2014-158517, mailed on Jun. 22, 2017. 14 pages of official Copy only.
Office Action Received for Japanese Patent Application No. 2014-158517, mailed on May 19, 2015, 5 pages (2 pages of English Translation and 3 pages of Official Copy).
Office Action received for Japanese Patent Application No. 2015-036444, mailed on Feb. 23, 2016, 3 pages of English translation only.
Office Action received for Japanese Patent Application No. 2015-526523, mailed on Jan. 25, 2017, 8 pages (5 pages of English Translation and 3 pages of Official Copy Only).
Office Action received for Japanese Patent Application No. 2016-143049, mailed on Apr. 24, 2017. 5 pages (2 pages of English Translation and 3 pages of Official copy).
Office Action received for Japanese Patent Application No. 2017-212658, mailed on Dec. 20, 2018, 10 pages (6 pages of English Translation and 4 pages of Official Copy).
Office Action received for Japanese Patent Application No. 2017-212658, mailed on Sep. 12, 2018, 8 pages (5 pages of English Translation and 3 pages of Official Copy).
Office Action received for Japanese Patent Application No. 2017-212659, mailed on Jul. 5, 2018, 2 pages (Official Copy Only).
Office Action received for Japanese Patent Application No. 2017-212659, mailed on Mar. 4, 2019, 2 pages (Official Copy Only).
Office Action received for Japanese Patent Application No. 2015-036444, mailed on Sep. 14, 2016, 5 pages (3 Pages of English Translation and 2 Pages of Official Copy).
Office Action received for Japanese Patent Application No. 2016-094326, mailed on Dec. 2, 2016, 4 pages (2 pages of English Translation and 2 pages Official Copy Only).
Office Action received for Japanese Patent Application No. 2016-094326, mailed on Jul. 6, 2017, 2 pages (Official Copy Only).
Operator's Manual Intravascular Lithotripsy (IVL) Generator and Connector Cable LBL 61876 Rev. E Mar. 2018, pp. 1-16.
Optical Coherence Tomography Assessment of the Mechanistic Effects of Rotational and Orbital Atherectomy in Severely Calcified Coronary Lesions, Catheterization and Cardiovascular Interventions, vol. 86, 2015, pp. 1024-1032.
Oral Argument *Cardiovascular Systems Inc.* vs. *Shockwave Medical Inc.* in Inter Partes Review No. IPR2019-00405, dated May 8, 2019, 35 pages.
Otsuka et al., "Has Our Understanding of Calcification in Human Coronary Atherosclerosis Progressed", Coronary Calcification, Apr. 2014, pp. 724-738.
Patent Owner Preliminary Response for U.S. Pat. No. 8,956,371, by the Patent Trial and Appeal Board dated Apr. 10, 2019, 79 pages.
Patent Owner Sur-Reply for U.S. Pat. No. 8,956,371, by the Patent Trial and Appeal Board dated May 24, 2019, 8 pages.
Patent Owner's Response Nov. 7, 2019, 70 pages.
Patent Owner's Response Case No. IPR2019-00409 Nov. 3, 2019, 65 pages.
Patent Owner's Updated Exhibit List for U.S. Pat. No. 8,956,371, by the Patent Trial and Appeal Board dated May 24, 2019, 7 pages.
Patent Owner's Sur-Reply for U.S. Pat. No. 8,956,371, by the Patent Trial and Appeal Board dated Mar. 20, 2020, Mar. 20, 2020, 53 pages.
Patent Owner's Updated Exhibit List for U.S. Pat. No. 8,956,371, by the Patent Trial and Appeal Board dated Mar. 20, 2020, 18 pages.
Patterson et al., (1985). "The Etiology and Treatment of delayed Bleeding following Percutaneous Lithotripsy," The Journal of Urology, 133:447-451.
Peripheral Diamondback 360 Peripheral OAS, Micro Crown, Patents, Cardiovascular Systems, Inc., 201 T, 6 pages.
Peripheral Intravascular Lithotripsy (IVL) Catheter—Instructions for Use (IFU) LBL 61932, Rev A Instructions for Use US Jan. 2018, pp. 1-5.
Peripheral Intravascular Lithotripsy (IVL) Catheter Instructions for Use (IFU) LBL 61959, Rev. B Instructions for Use Jun. 2018, pp. 1-7.
Peripheral IVL Case Setup and Execution Shockwave Medical Inc., Available Online at <http://shockwavemedical.com/wp-content/uploads/2018/12/PAD-IVL-Case-Set-Up.pdf>, pp. 1-11.
Petition for Inter Partes Review for U.S. Pat. No. 8,956,371, issued on Feb. 17, 2015, 75 pages.
Petitioner Power of Attorney for U.S. Pat. No. 8,956,371, dated Dec. 6, 2018, pp. 1-2.
Petitioner's Reply Brief Case IPR2019-00405 Feb. 21, 2020, 65 pages.
Petitioner's Reply to Patent Owner's Preliminary Response for U.S. Pat. No. 8,956,371, by the Patent Trial and Appeal Board dated May 15, 2019, 7 pages.
Press Release: Shockwave Medical Reports Fourth Quarter and Full Year 2019 Financial Results and Provides Full Year 2020 Financial Outlook, Mar. 4, 2020, 7 pages.
Press Release: St. Francis Participates in Landmark Study Using Sonic Pressure Waves to Treat Heart Blockages, Catholic Health, Jan. 17, 2019, 5 pages.
Publicly available Professional & Educational Background Summary for Clifton Alferness Exhibit 1229 2013, 3 pages.

(56) References Cited

OTHER PUBLICATIONS

Publicly available Professional & Educational Background Summary for Daniel Hawkins Exhibit 1226, 2018, 2 pages.
Publicly available Professional & Educational Background Summary for Guy Levy Exhibit 1253 2019, 2 pages.
Publicly available Professional & Educational Background Summary for John Adams Exhibit 1221, 2009, 2 pages.
Publicly available Professional & Educational Background Summary for Krishna Bhatta Exhibit 1251 2005, 2 pages.
Publicly available Professional & Educational Background Summary for Marat Izrailevich Lerner 2020, 3 pages.
Publicly available Professional & Educational Background Summary for Marat Lerner 2008-2020, 4 pages.
Publicly available Professional & Educational Background Summary for Naoki Uchiyama 2020, 2 pages.
Publicly available Professional & Educational Background Summary for Ralph de la Torre Exhibit 1252 2010, 2 pages.
Publicly available Professional & Educational Background Summary for Robert Mantell Exhibit 1256 2000, 2 pages.
Publicly available Professional & Educational Background Summary for Stepan Khachin 2008-2020, 3 pages.
Publicly available Professional & Educational Background Summary for Valery Diamant Exhibit 1257 2017, 2 pages.
Redline of Shockwave Provisional to Utility, pp. 1-6.
Response to Final Office Action received for U.S. Appl. No. 12/482,995, filed Sep. 19, 2011 Sep. 19, 2011, 20 pages.
Ricks, Delthia Long Island Doctors Using Sound Waves to Loosen Calcium Deposits from Arteries, Restore Blood Flow News/Health, Available Online at <https://www.newsday.com/news/health/calcium-treatment-st-francis-hospital-1.27314331> Feb. 15, 2019, p. 1-4.
Rocha-Singh, et al. Peripheral Arterial Calcification: Prevalence, Mechanism, Detection, and Clinical Implications Catheterization and Cardiovascular Interventions, vol. 86 2014 pp. E212-E220.
Rosenschein et al., (1992). "Shock-Wave Thrombus Ablation, a New Method for Noninvasive Mechanical Thrombolysis," The American Journal of Cardiology, 70:1358-1361.
Sakes et al., (2016). "Crossing Total Occlusions: Navigating Towards Recanalization," Cardiovascular Engineering and Technology, 7(2):103-117.
Salunke et al., (2001). "Compressive Stress-Relaxation of Human Atherosclerotic Plaque," J Biomed Mater, 55:236-241.
Sasaki et al., (2015). New Insight into Scar-related Ventricular Tachycardia Circuits in Ischemic Cardiomyopathy: Fat Deposition after Myocardial Infarction on Computed Tomography, Heart Rhythm, 12(7):1508-1518.
Schenkman, Noah Ureter Anatomy WebMD LLC, Emedicine. medscape.com, Jul. 10, 2013, 8 pages.
Second Declaration of Natalie J. Grace dated May 24, 2019, pp. 1-2.
Shlofmitz et al., (2019). "Orbital Atherectomy: A Comprehensive Review," Interv Cardiol Clin, 8(2):161-171.
ShockwaveMedical.com Intravascular Lithotripsy (IVL) Available Online at <https://shockwavemedical.com/technology/intravascular-lithotripsy-ivl/?country=Egypt> 2019, pp. 1-4.
Simpson et al., (1962). "A New Catheter System for Coronary Angioplasty," The American Journal of Cardiology, 49:1216-1222.
Smith et al., (1992). "Microwave Thermal Balloon Angioplasty in the Normal Rabbit," American Heart Journal, 123(6):1516-1521.
Sokol (2011). "Clinical Anatomy of the Uterus, Fallopian Tubes, and Ovaries," Glob. Libr. Women's Med., pp. 1-12.
Soukas, "Deposition Transcript (compressed) of Peter Soukas, Cases:--IPR2019-00405, IPR2019-00408, IPR2019-00409," Dec. 30, 2019, 10 pages.
Stephens, William, "Deposition Transcript (compressed) of William Patrick Stephens Case No. IPR2019-00408," Jan. 22, 2020, 55 pages.
Supplemental Declaration of Dr. Morten Olgaard Jensen Case IPR2019-00405 Feb. 21, 2020, 136 pages.
Tanaka et al., (2001). "A New Radiofrequency Thermal Balloon Catheter for Pulmonary Vein Isolation," Journal of the American College of Cardiology, 38(7):2079-2086.
Thiem et al., (2018). "The 12-Month Results of the EffPac Trial," Journal of Vascular Surgery, 68(55):e122-e123.
Third Party Preissuance Submission for U.S. Appl. No. 15/817,073, filed Aug. 5, 2019, 3 pages.
Third Party Preissuance Submission for U.S. Appl. No. 16/436,186, filed on Jan. 10, 2020, 3 pages.
Third-Party Submission Under 37 CFR 1.290 Concise Description of Relevance for U.S. Appl. No. 15/817,073, filed Aug. 5, 2019, 3 pages.
Top Cardiovascular Innovation Award Cardiovascular Research Technologies (CRT) 2015, 1 page.
WebMD.com Definition of 'Angioplasty' Available Online at <https://www.webmd.com/heart-disease/heart-failure/qa/what-is-the-definition-of-angioplasty> Oct. 29, 2017, pp. 1-2.
Weide, Daniel Deposition Transcript (compressed) of Daniel van der Weide, Ph.D. Exhibit 1203, Case No. IPR2019-00408, U.S. Pat. No. 9,642,673 B2 Jan. 13, 2020, 94 pages.
Wells Fargo Securities LLC SWAV: Initiating With a Market Perform Rating Shockwave Medical Inc. Apr. 1, 2019, pp. 1-34.
Written Opinion received for PCT Patent Application No. PCT/US2012/023172, mailed on Sep. 28, 2012, 4 pages.
Written Opinion received for PCT Patent Application No. PCT/US2009/047070, mailed on Jan. 19, 2010, 5 pages.
Yamamoto et al., (2018). "Effect of orbital atherectomy in calcified coronary artery lesions as assessed by optical coherence tomography," Catheter Cardiovasc Interv, 93(7):1211-1218.
Zhong et al., (1997). "Publication Information—Transient Oscillation of Cavitation Bubbles Near Stone Surface During Electrohydraulic Lithotripsy," Journal of Endourology, 11, 1 page.
Zhong et al., (1997). "Transient Oscillation of Cavitation Bubbles Near Stone Surface During Electrohydraulic Lithotripsy," Journal of Endourology, 11(1):55-61.
International Search Report and Written Opinion received for PCT Patent Application No. PCT/US2021/071938, mailed on Jan. 18, 2022, 13 pages.
Non-Final Office Action received for U.S. Appl. No. 16/436,186, mailed on Jun. 10, 2022, 14 pages.
Notice of Allowance received for U.S. Appl. No. 17/025,866, mailed on Jul. 7, 2022, 3 pages.
Notice of Allowance received for U.S. Appl. No. 16/436,186, mailed on Apr. 22, 2022, 8 pages.
Notice of Allowance received for U.S. Appl. No. 16/436,186, mailed on Nov. 2, 2022, 7 pages.
Notice of Allowance received for U.S. Appl. No. 16/436,186, mailed on Nov. 10, 2022, 4 pages.
Notice of Allowance received for Chinese Patent Application No. 201980041113.7, mailed on Oct. 29, 2024, 7 pages. English translation.
Notice of Acceptance received for Australian Patent Application No. 2019290401, mailed on Feb. 14, 2025, 3 pages.
Notice of Allowance received for U.S. Appl. No. 17/477,483, mailed on Mar. 6, 2024, 2 pages.
Notice of Allowance received for U.S. Appl. No. 17/477,483, mailed on Feb. 9, 2024, 2 pages.
Notice of Allowance received for U.S. Appl. No. 17/477,483, mailed on Feb. 1, 2024, 2 pages.
Notice of Allowance and Examiner Interview Summary Record received for U.S. Appl. No. 17/477,483, mailed on Jan. 22, 2024, 10 pages.
Examiner Interview Summary Record received for U.S. Appl. No. 17/477,483, mailed on Oct. 2, 2023, 3 pages.
Office Action received for U.S. Appl. No. 17/477,483, mailed on Jun. 22, 2023, 22 pages.
Notice of Allowance received for U.S. Appl. No. 18/104,170, mailed on Sep. 5, 2024, 4 pages.
Notice of Allowance and Examiner Interview Summary Record received for U.S. Appl. No. 18/104,170, mailed on Aug. 14, 2024, 8 pages.
Office Action received for U.S. Appl. No. 18/104,170, mailed on Apr. 24, 2024, 9 pages.
Requirement for Restriction received for U.S. Appl. No. 18/104,170, mailed on Feb. 28, 2024, 5 pages.

(56) References Cited

OTHER PUBLICATIONS

Notice of Allowance and Search Report received for Chinese Patent Application No. 202080081128.9, mailed on Oct. 15, 2024, 6 pages. English translation.

Office Action received for European Patent Application No. 21805823.8, mailed on Feb. 7, 2025, 4 pages.

Office Action received for Australian Patent Application No. 2020354380, mailed on May 19, 2025, 5 pages.

* cited by examiner

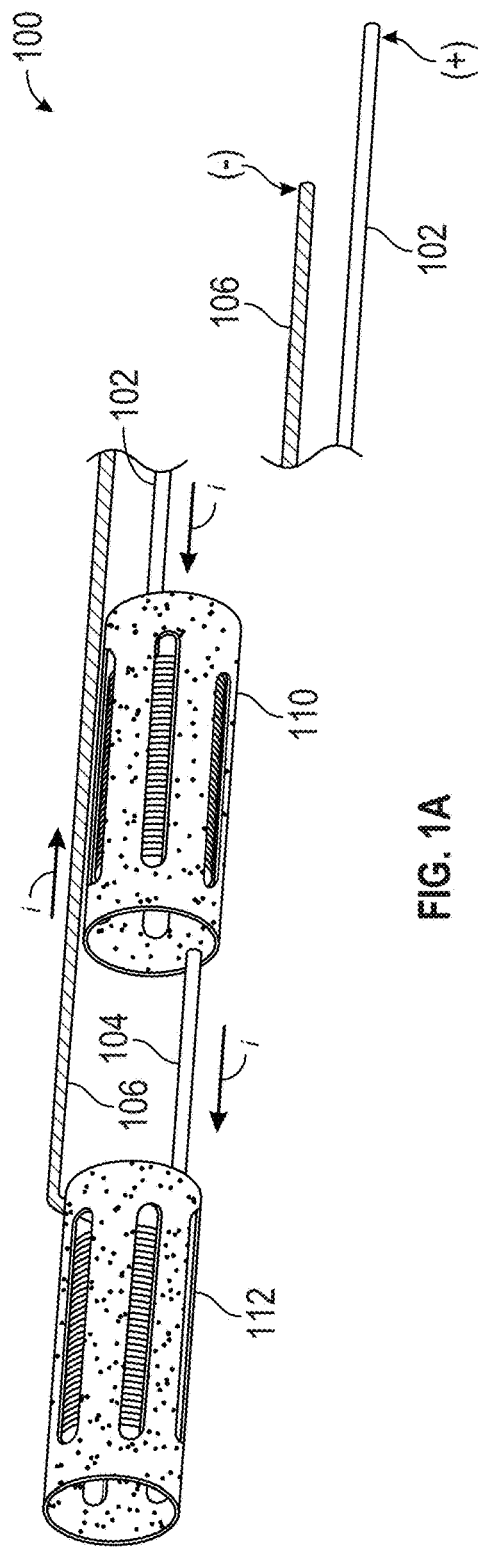
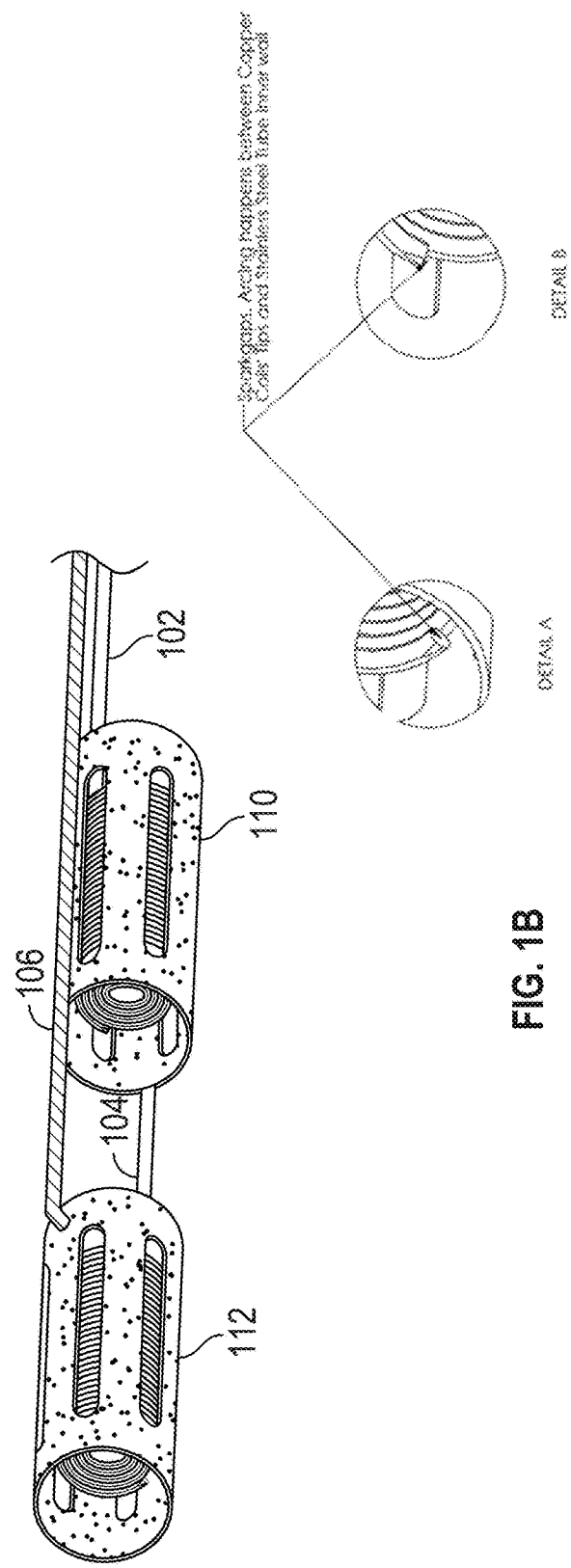
FIG. 1A
FIG. 1B

SYSTEM FOR TREATING THROMBUS IN BODY LUMENS

CROSS-REFERENCE TO RELATED APPLICATIONS

This application is a continuation of U.S. patent application Ser. No. 17/025,866, entitled "SYSTEM FOR TREATING THROMBUS IN BODY LUMENS," filed on Sep. 18, 2020, which claims priority to U.S. Provisional Patent Application No. 62/904,974, entitled "SYSTEM FOR TREATING THROMBUS IN BODY LUMENS," filed on Sep. 24, 2019, the content of each of which is hereby incorporated by reference in its entirety.

FIELD OF THE DISCLOSURE

The present disclosure relates generally to thrombectomy devices, and more specifically, to thrombectomy devices designed to generate cavitation bubbles for reducing or removing thrombus from the vascular system of a patient.

BACKGROUND

Thrombectomy devices are designed to reduce clot burden and partially or completely remove a blood clot (i.e., thrombus) from the vascular system of a patient. Currently, the mechanism of removing thrombus in most thrombectomy devices is mechanical or involves a combination of the plasminogen activator ("tPA") treatment and a mechanical process. Some of these devices use ultrasound for the purpose of diffusing tissue plasminogen activator (tPA). It does this by increasing permeability in thrombus structure which exposes more sites to which thrombolytic agents can bind. These devices all have deficiencies, as they provide an undesirably slow rate of clot removal, which typically requires an overnight stay in the hospital. Further, these devices tend to be expensive, bulky, and difficult to operate. Further still, these devices can involve a high loss of blood in the patient.

Accordingly, a need exists for a device that treats blood clots without the use of drugs (e.g., tPA) and provides a cost-effective and time-efficient solution for treating thrombus.

BRIEF SUMMARY

The present invention relates to thrombectomy devices designed to generate cavitation bubbles for reducing or removing thrombus from the vascular system of a patient. Because embodiments of the present invention do not require the use of drugs (e.g., tPA) and can work quickly (e.g., less than 2 hours), the present invention provides a cost-effective and efficient solution for treating thrombus.

In one embodiment, the invention provides a device for generating cavitation bubbles. An exemplary catheter comprises: an emitter assembly comprising at least one emitter; wherein each emitter comprises an electrode pair, and wherein each emitter is configured to generate a plurality of cavitation bubbles when a voltage is applied to the pair of electrodes; an infusion lumen formed by at least a portion of an outer wall of the catheter, the infusion lumen configured to receive a conductive fluid, wherein the emitter assembly is housed within the infusion lumen, wherein a distal segment of the infusion lumen includes a plurality of holes on the portion of the outer wall of the catheter, and wherein the plurality of holes are configured to release the conductive fluid and the plurality of cavitation bubbles out of the catheter to treat thrombus at a treatment site; an aspiration lumen formed in the catheter and including a plurality of aspiration ports at the distal segment thereof.

In some embodiments, the emitter assembly comprises: an elongated conductive tube; an insulated wire having a helically coiled portion at an end of the insulated wire, wherein the coiled portion includes an exposed tip, and wherein the coiled portion is positioned within the elongated conductive tube; and wherein, when a voltage is applied across the insulated wire and the elongated conductive tube, a current is configured to flow from the exposed distal tip of the insulated wire to the elongated conductive tube to generate the plurality of cavitation bubbles.

In some embodiments, the elongated conductive tube comprises a slot, and wherein the current is configured to flow from the exposed distal tip of the insulated wire to an edge of the slot.

In some embodiments, the current is configured to flow from the exposed distal tip of the insulated wire to an inner wall of the elongated conductive tube.

In some embodiments, the emitter assembly comprises a first wire and a second wire, wherein at least a portion of insulation is removed from a portion of the first wire, wherein at least a portion of insulation is removed from a portion of the second wire, wherein the portion of the first wire is interleaved with the portion of the second wire, wherein, when a voltage is applied across the first wire and the second wire, a current is configured to flow from the first wire to the second wire to generate the plurality of cavitation bubbles.

In some embodiments, the emitter assembly comprises: a conductive sheath, and an insulated wire having an exposed tip, wherein a current is configured to flow from the exposed distal tip of the insulated wire to the conductive sheath to generate the plurality of cavitation bubbles.

In some embodiments, the plurality of holes are arranged in three rows spaced 120 degrees apart on the outer wall of the catheter.

In some embodiments, the infusion lumen is Y-shaped.

In some embodiments, a pump is configured to deliver a continuous flow of conductive fluid to the emitter assembly through the infusion lumen.

In some embodiments, the continuous flow of conductive fluid flushes debris into the aspiration lumen via the plurality of aspiration ports.

In some embodiments, a pump is configured to apply suction at a proximal end of the aspiration lumen to suck debris into the aspiration lumen via the plurality of aspiration ports.

In some embodiments, an aspiration port of the plurality of aspiration ports is larger than a hole of the plurality of holes.

In some embodiments, the catheter further comprises a guide wire lumen for accommodating a guide wire.

In some embodiments, the catheter further comprises a distal cap configured to seal a distal end of the catheter, wherein the distal cap comprises a hole for accommodating the guide wire.

In some embodiments, the catheter further comprises an electrical wire lumen for accommodating one or more wires of the emitter assembly.

In some embodiments, the voltage is between 500V and 1200V

In some embodiments, the repetition rate of the applied voltage is adjustable between 25 Hz and 200 Hz.

In some embodiments, the electrode pair comprises a spark gap between electrodes of the pair, the spark gap being less than 0.005 inches.

DESCRIPTION OF THE FIGURES

FIG. 1A depicts an exemplary emitter assembly, in accordance with some embodiments.

FIG. 1B depicts an exemplary emitter assembly, in accordance with some embodiments.

DETAILED DESCRIPTION

Figure 2A:
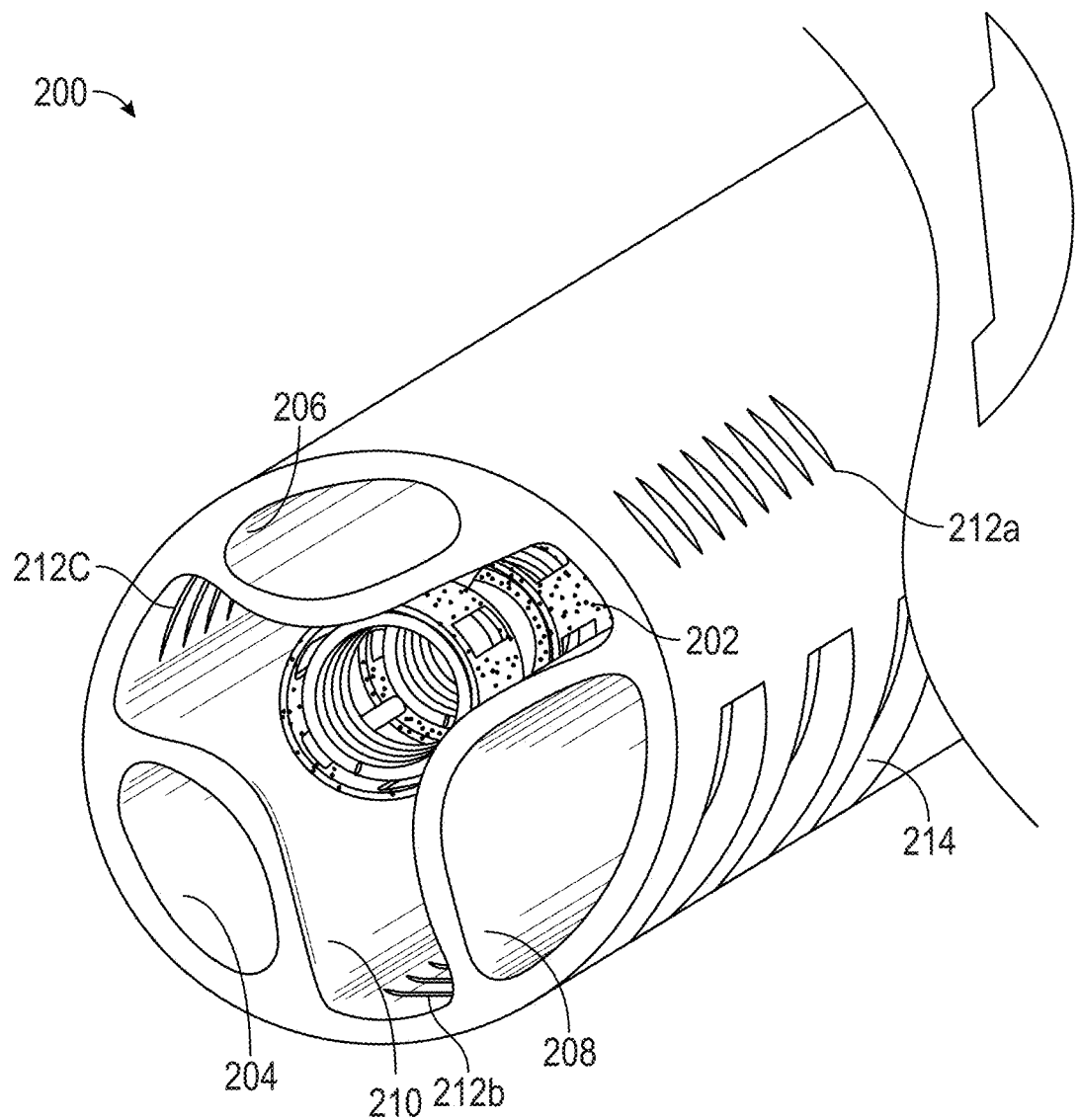
FIG. 2A depicts a cross-sectional view of an exemplary catheter housing an emitter assembly, in accordance with some embodiments.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Described herein are exemplary systems and methods for reducing or removing thrombus from the vascular system of a patient by generating cavitation bubbles via a voltage source. In according with some embodiments, the treatment system includes a catheter and one or more emitters housed within the catheter. The catheter is advanced within the body lumen (e.g., a blood vessel) to the treatment site (e.g., via a guide wire). Each emitter includes electrodes that, when connected to a relatively low-voltage and high-PRF (pulse repetition rate) generator, form plasma arcs that in turn lead to a large amount of cavitation bubbles forming and collapsing. In some embodiments, the catheter comprises one or more rows of cavitation holes for releasing the cavitation bubbles in an omnidirectional manner. The cavitation bubbles create mechanical vibrations, turbulence, jets, and/or forceful collapses to weaken and break the fibrin fiber network, thus reducing and removing thrombus.

The present invention is distinct from an electrohydraulic lithotripsy. The voltage at each emitter (i.e., across the spark gap) is lower than an intravascular lithotripsy ("IVL") treatment. In some embodiments, the voltage of the generator is adjusted between 500V to 1200V, and the repetition rate is adjusted between 25 Hz to 200 Hz. In order to maintain the breakdown voltage, the spark gap at the emitter (e.g., a spark gap formed between two electrodes of an electrode pair) is sufficiently small to allow a spark. In some embodiments, the gap is less than 0.005 inches. Further, the energy being delivered is lower than IVL, thus the acoustic power is generally not enough to generate pressure amplitude from any shock wave.

FIG. 1A depicts an exemplary emitter assembly 100, in accordance with some embodiments. The emitter assembly 100 comprises two conductive elongated tubes 110 and 112. Each elongated tube has a plurality of longitudinal slots to facilitate the generation cavitation bubbles, as discussed below. Further, the emitter assembly 100 comprises three wires 102, 104, and 106. In some examples, the elongated tubes can be stainless steel hypotubes, and the wires can be polyimide-insulated copper wires.

The first insulated wire 102 comprises a helically coiled portion at its distal end, which is placed within the first elongated tube 110. In some embodiments, the helically coiled portion is bonded to the inner wall of the elongated tube 110 with adhesive (e.g., epoxy or cyanoacrylate adhesive). Similarly, the second insulated wire 104 comprises a helically coiled portion at its distal end, which is placed within the second elongated tube 112. The third insulated wire 106 has a distal end that is connected (e.g., welded) to the second elongated tube 112. Further, the proximal end of the second insulated wire 104 is connected (e.g., welded) to the first elongated tube 110.

When the emitter assembly 100 is connected to a voltage source, a current traverses through the two elongated tubes and three wires to generate cavitation bubbles at two locations. With reference to FIG. 1A, the proximal end of the first wire 102 is connected to a positive port of a voltage generator (not depicted) and the proximal end of the third wire 106 is connected to a negative portion of the voltage generator. The generator delivers energy in continuous pulse mode or in the series of short bursts. Accordingly, a current i traverses the emitter assembly as indicated by the arrows. As shown, the current, i, traverses from the proximal end of the first insulated wire 102 toward its distal coiled portion. At the distal end of the first insulated wire 102, the conductive core of the wire is exposed, thus allowing the current to traverse from the distal end of the wire 102 to the first elongated tube 110. The exposed distal end of the first wire 102 and the first elongated tube 110 form a first electrode pair for generating cavitation bubbles.

The current i further traverses from the first elongated tube 110 to the proximal end of the second insulated wire 104, and then to the distal coiled portion of the second insulated wire 104. At the distal end of the second insulated wire 104, the conductive core of the wire is exposed, thus allowing the current to traverse from the distal end of the wire 104 to the second elongated tube 112. The exposed distal end of the second wire 104 and the second elongated tube 112 form a second electrode pair for generating cavitation bubbles. The current i then returns to the voltage generator via the third insulated wire 106.

As the current i traverses from the distal coiled portion of a wire to the elongated tube enclosing the coiled portion, a plurality of plasma arcs are formed between the exposed distal end of the wire and an inner surface of the elongated tube. Plasma arcs lead to cavitation bubbles in a controlled fashion (one at a time, at a particular rate), which in turn lead to mechanical vibrations, and other bubble dynamics-related effects such as collapses, turbulence, jetting, etc. in the conductive fluid (e.g., via the expansion and collapse of the bubbles). The mechanical vibrations serve to reduce or remove the thrombus. Cavitation has been known to weaken the fibrin network crosslink which is the base structure of the thrombus. Combination of mechanical vibrations and bubble cavitation can be effective in thrombolysis. As compared to the generators used in the prior art shock wave generation systems mentioned above, the generator for this system is configured to generate lower-voltage pulses at a higher pulse repetition rate in order to minimize the strength of any shock wave and optimize and maximize bubble growth and collapse. For example, in the prior art systems, each pulse might be about 3000 volts with a 1 Hz repetition rate. In embodiments of this system, the voltage of the voltage pulses is adjusted between 500V to 1200V; repetition rate of the voltage pulses is adjusted between 25 Hz to 200 Hz; and pulse duty cycle is adjusted between 10-50%. These parameters can be varied based on the blood clot condition.

FIG. 1B depicts the exemplary emitter assembly 100 from a different angle, showing the distal coiled portions of the two wires, in accordance with some embodiments. As the plasma arcs cause erosion to the electrodes in operation, the helically coiled wire portions of wires 102 and 104 can erode and shorten over time. Depending on where the distal end of the wire is, the spark gap (i.e., where plasma arcs are formed) can be between the distal end of the wire and the inner wall of the elongated tube (as shown in Detail A view), or between the distal end of the wire and an edge of a slot of the elongated tube (as shown in Detail B view). Note that as the coiled wire portion erodes, the location of the generation of the cavitation bubbles will change. In the illustrated embodiment, the location of the generation of the cavity bubbles will rotate circumferentially about the periphery of the conductive tubes 110 and 112.

Additional details on electrode pairs formed by a coiled wire and an elongated tube, along with possible variations, are provided in assignee's prior filing US Publication No. 2019/0388110 titled "SYSTEM FOR TREATING OCCLUSIONS IN BODY LUMENS," which is incorporated by reference. It should be appreciated that, while FIGS. 1A-B depict a emitter assembly comprising two emitters connected in a series driven by one voltage source, the emitter assembly can comprise any number of emitters arranged in any configuration driven by one or more voltage sources.

FIG. 2A depicts a cross-sectional view of an exemplary catheter 200 comprising a number of lumens, in accordance with some embodiments. The catheter 200 comprises a Y-shaped infusion lumen 210 and three oval-shaped lumens: guide wire lumen 204, electrical wire lumen 206, and aspiration lumen 208. As shown in FIG. 2A, the oval-shaped lumens 204, 206, 208 are spaced approximately 120 degrees apart along the outer wall of the catheter and are formed at least partially from the outer wall of the catheter. The inner edges of the guide wire lumen 204, electrical wire lumen 206, and aspiration lumen 208 define the outer edges of the central Y-shaped infusion lumen 206.

The Y-shaped infusion lumen 210 houses an emitter assembly 202, which can be any of the emitter assemblies described herein (e.g., 100, 300, 400). As discussed above, the emitter assembly 202 comprises a number of elongated conductive tubes and wires, forming a number of emitters (or electrode pairs). In some embodiments, the emitter assembly 202 is placed in the distal segment of the catheter.

The Y-shaped infusion lumen 210 can further be used to deliver an ionic solution (e.g., a conductive solution such as saline or saline mixed with a contrast medium) from a pump to the emitter assembly 202. When the emitter assembly 202 is connected to a voltage source, cavitation bubbles can be generated via the conductive fluid at multiple locations along the catheter.

The Y-shaped infusion lumen further comprises multiple rows of cavitation holes for releasing the cavitation bubbles. In the depicted example, three rows of cavitation holes 212a, 212b, and 212c are spaced 120 degrees apart. As shown in FIG. 2A, the cavitation holes 212a, 212b, 212c could include a plurality of lateral slots extending along a portion of the circumference of the distal end of the catheter. The cavitation holes could be positioned to maximize the release of cavitation bubbles, e.g., positioned directly above the first elongated tube, the second elongated tube, or another element of the emitter assembly. As such, the cavitation bubbles from the emitter assembly are carried out radially by the pumped flow of the ionic solution through the rows of cavitation holes to the thrombus.

The aspiration lumen 208 can be used to remove debris (e.g., metals, bubbles) and thrombus fragments from the treatment site. As shown, the aspiration lumen 208 comprises a series of aspiration ports 214. The aspiration ports 214 are generally larger than the cavitation holes 212. As more conductive fluid is injected, debris and thrombus fragments are flushed toward the aspiration lumen and carried away from the treatment site. Additionally or alternatively, suction can be provided at the proximal end of the aspiration lumen 208. The debris and thrombus fragments can be sucked into the aspiration ports 214 and carried away from the treatment site via the flow of conductive fluid. The rapid removal of debris helps to refresh the cavitation.

The electrical wire lumen 206 can be used to accommodate one or more wires of the emitter assembly 202. For example, the wire connecting the distal portion of the emitter assembly to the negative port of the voltage generator (e.g., wire 106) can extend through the electrical wire lumen 206 for better insulation. The wire lumen 206 may also carry one or more additional wires, for instance, wire 102 connecting the proximal portion of the emitter assembly to a positive port of the voltage generator. The guide wire lumen 204 can be used to accommodate a guide wire and may be shaped to carry a guidewire having a diameter between approximately 0.014 inches and approximately 0.035 inches. The guide wire is used to advance the catheter 200 to the treatment site.

Figure 2B:
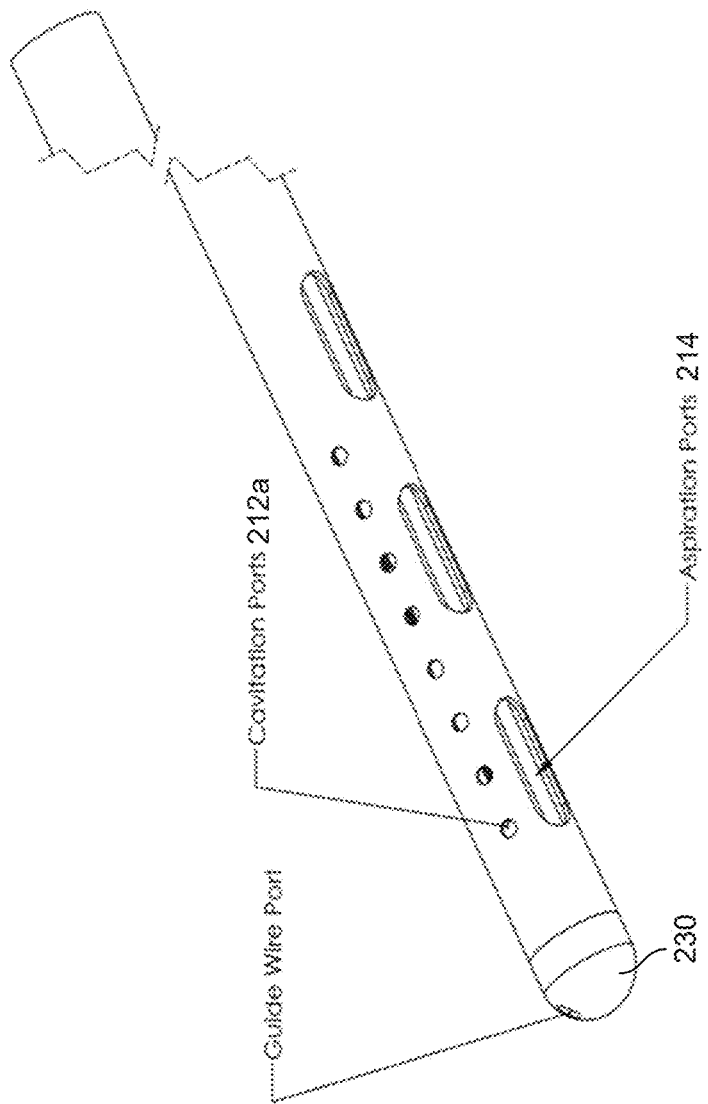
FIG. 2B depicts another exemplary catheter housing an emitter assembly, in accordance with some embodiments.

FIG. 2B depicts another exemplary catheter housing an emitter assembly, in accordance with some embodiments. As shown, the catheter includes a cap 230, which includes a guide wire port for receiving a guidewire (e.g., a guidewire carried in a guidewire lumen of the catheter during advancement of the catheter). Further, the shape and location of the aspiration ports and cavitation holes are different in the embodiment illustrated in FIG. 2A. For instance, as shown in FIG. 2B, the aspiration ports can formed as longitudinal slots sized to allow debris from cavitation to escape through the aspiration ports. The cavitation ports could include a plurality of approximately circular holes in the catheter housing (i.e., the outer wall of the catheter) allowing access to the Y-shaped infusion lumen.

The catheter in FIGS. 2A-B can be used in conjunction with a pump. In some embodiments, the pump delivers an ionic solution (i.e., a conductive solution such as saline or saline mixed with a contrast medium) via the infusion lumen to the catheter tip where the cavitation takes place. The pump or an auxiliary pump also aspirates debris away from the thrombus region. The infusion flow can be synchronized to the emitters' power delivery to ensure the adequate ionic solution around the emitters. The aspiration flow and infusion flow can be synchronized to maintain the pressure equilibrium at the treatment site. In some examples, the flow of saline or saline/angiographic contrast medium is adjusted to avoid over-heating issues and control treatment efficiency and rate.

In some embodiments, additional components are included in the treatment system, such as a proximal balloon for trapping debris produced by the emitter, a visualization system and/or a steering system for properly navigating (e.g., side branches) and placing the catheter, etc. Additional details of the treatment system are provided in US Publication No. 2019/0388110, referenced above and incorporated herein by reference.

In some embodiments, the procedure can take around 30 minutes, during which the emitter assembly 202 continuously generates cavitation bubbles. These operation parameters (e.g., voltage, repetition rate, or pulse duty cycle of the voltage pulses) can be set based on the characteristics of the blood clot (e.g., size of the clot, age of the clot, composition of the clot, softness of the clot, arterial or venous location of the clot, platelet content of the clot, fibrin content of the clot, or some other attribute of the clot) and/or characteristics of the patient (e.g., age or preexisting medical condition of the patient). In some embodiments, after the procedure, a post-operation minimally invasive procedure (e.g., treatment of bleeding, thrombus reforming) can be performed.

Figure 3:
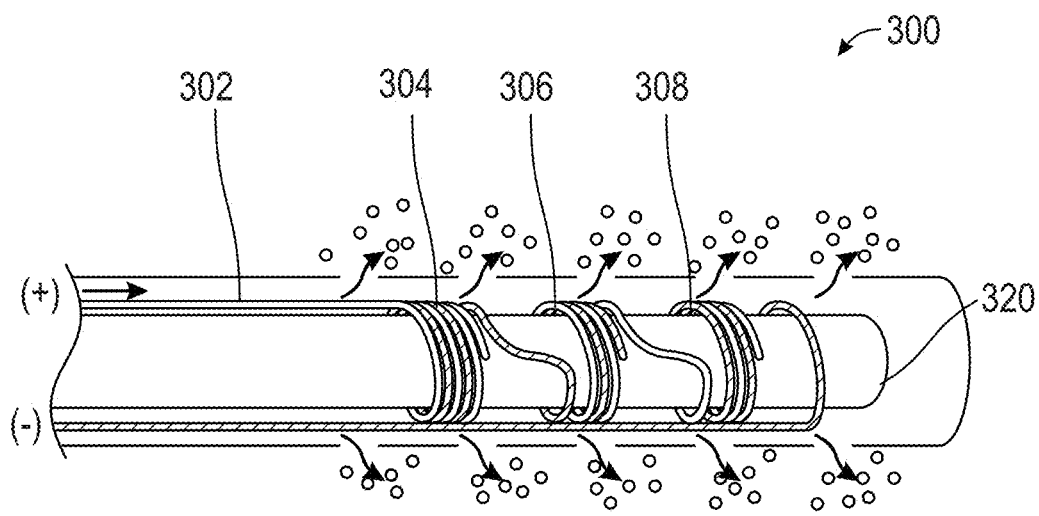
FIG. 3 depicts another exemplary emitter assembly, in accordance with some embodiments.

FIG. 3 depicts another exemplary emitter assembly housed in a catheter 300, in accordance with some embodiments. The emitter assembly includes four wires 302, 304, 306, and 308. Each of the four wires includes a portion that is wrapped helically around a shaft 320 (e.g., guide wire shaft having a lumen to carry a guidewire), and together the four wires form three interleaved wire portions. An interleaved wire portion may comprise a plurality (i.e., 2 or more) of portions of wires configured in an interleaved manner. For example, an interleaved wire portion may include a portion of a wire coiled with a portion of another wire. In some variations, the wires and interleaved wire portions are configured in series. For example, the first wire 302 may be electrically coupled to a positive terminal of a voltage source. The first interleaved wire portion may comprise a portion of the first wire 302 interleaved with a first portion of the second wire 304. The first wire 302 may have an electrical voltage or potential that is more positive than the second wire 304. Similarly, the second interleaved wire portion 304 may comprise a second portion of the second wire 304 interleaved with a first portion of the third wire 306. The second wire 304 may have an electrical voltage or potential that is more positive than that of the third wire 306. And the third interleaved wire portion 306 may comprise a second portion of the third wire 306 and a portion of the fourth wire 308. The third wire 306 may have an electrical voltage or potential that is more positive than that of the fourth wire 308. The fourth wire 308 may be electrically coupled to a negative terminal of a voltage source.

In the illustrated embodiment in FIG. 3, each interleaved wire portion includes at least one pair of electrodes. Electrodes of each pair are defined by removing small regions of insulation from adjacent portions of interleaved wires. When a high voltage is delivered to the wires when the wires are surrounded by a conductive fluid (i.e., when conductive fluid is flowed through the wire lumen), an electrohydraulic discharge generates plasma that generates a cavitation bubbles at the arc-generating region across the electrodes. Additional details of the operation and possible variations of the emitter assembly can be found in assignee's prior filing U.S. Pub. No. 2018/0098779, titled "AORTIC LEAFLET REPAIR USING SHOCK WAVE APPLICATORS," which is incorporated by reference.

In the illustrated embodiment in FIG. 3, the emitter assembly is housed within a catheter 300, for instance, any of the catheters described with respect to FIGS. 2A-B. As shown, the catheter comprises rows of cavitation holes (e.g., longitudinal or lateral slots or circular holes) positioned over the emitters for releasing the cavitation bubbles in an omnidirectional manner.

Figure 4:
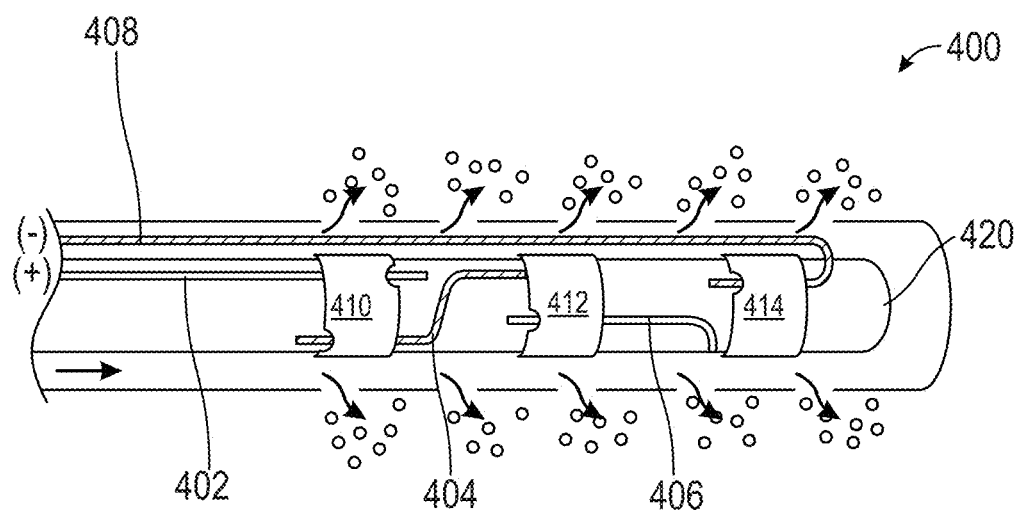
FIG. 4 depicts another exemplary emitter assembly, in accordance with some embodiments.

FIG. 4 depicts another exemplary emitter assembly housed in a catheter 400, in accordance with some embodiments. The emitter assembly includes four wires 402, 404, 406, and 408, as well as three conductive sheaths 410, 412, and 414. The conductive sheaths are wrapped circumferentially around a portion of a shaft 420 (e.g., a guide wire shaft having a lumen for carrying a guidewire). An outer electrode is formed by a conductive sheath, and an inner electrode is formed by removing a portion of an insulated wire (e.g., cutting a hole in the insulating layer near the end of the wire) to expose an electrically conductive portion of the insulated wire. The inner electrode is placed a controlled distance apart from the side edge of the conductive sheath to allow for a reproducible arc for a given current and voltage. In operation, plasma arcs may be formed across the inner electrode and the side edge of the conductive sheath.

In the illustrated embodiment in FIG. 4, the emitter assembly is connected to a voltage source by way of a first wire 402 and a fourth wire 408, for instance, with the first wire connected to a positive port and the fourth wire connected to a negative port ground. A current traverses from the first wire 402 to the first conductive sheath 410, to a second wire 404, to the second conductive sheath 412, to the third wire 406, to the third conductive sheath 414, to the fourth wire 408, and to the negative port of the voltage source. Accordingly, the emitter assembly generates cavitation bubbles at six locations (i.e., the two side edges of each conductive sheath where the sheath forms electrode pairs with the insulation removed portions of the wires). Additional details of the operation and possible variables of the emitter assembly can be found in assignee's prior filing U.S. Pub. No. 2019/0150960, titled "LOW PROFILE ELECTRODES FOR A SHOCK WAVE CATHETER," which is incorporated by reference.

In the illustrated embodiment in FIG. 4, the emitter assembly is housed within a catheter 400, for instance, any of the catheters described with respect to FIGS. 2A-B. As shown, the catheter comprises rows of cavitation holes (e.g., longitudinal or lateral slots or circular holes) positioned over the emitters for releasing the cavitation bubbles in an omnidirectional manner.

It will be understood that the foregoing is only illustrative of the principles of the invention, and that various modifications, alterations and combinations can be made by those skilled in the art without departing from the scope and spirit of the invention. Any of the variations of the various cavitation devices disclosed herein can include features described by any other cavitation devices or combination of shock wave devices herein. Furthermore, any of the methods can be used with any of the cavitation devices disclosed. Accordingly, it is not intended that the invention be limited, except as by the appended claims. For all of the variations described above, the steps of the methods need not be performed sequentially

The invention claimed is:

1. A catheter for use in a lumen of a vascular system, the catheter comprising:
   an emitter assembly comprising at least one emitter that includes an elongated conductive tube and a wire at least partially disposed within the elongated conductive tube such that an uninsulated portion of the wire and the elongated conductive tube form an electrode pair configured to generate plasma arcs when voltage pulses are applied across the electrode pair;
   an outermost wall defining an infusion lumen configured to receive a conductive fluid, and
   at least one cavitation hole extending through the outermost wall and opening into the infusion lumen, the at least one cavitation hole being aligned with the electrode pair, wherein the electrode pair is positioned in the conductive fluid when the conductive fluid is received in the infusion lumen such that the plasma arcs create a plurality of cavitation bubbles in the conductive fluid, and the at least one cavitation hole is sized and shaped to direct the plurality of cavitation bubbles out of the catheter to a treatment region of the lumen of the vascular system.

2. The catheter of claim 1, further comprising a guidewire lumen sized to carry a guidewire, the guidewire lumen extending parallel to the infusion lumen.

3. The catheter of claim 2, further comprising an aspiration lumen separate from and extending parallel to the infusion lumen and the guidewire lumen and at least one port defined in the outermost wall and opening into the aspiration lumen, wherein the at least one port is positioned to receive debris and tissue fragments from the treatment region of the lumen of the vascular system via flow of the conductive fluid.

4. The catheter of claim 3, wherein the at least one cavitation hole has an outer opening located at a first circumferential position on the outermost wall, and the at least one port has an outer opening located at a second circumferential position on the outermost wall spaced apart from the outer opening of the at least one cavitation hole.

5. The catheter of claim 4, wherein the outer opening of the at least one port is larger than the outer opening of the at least one cavitation hole.

6. The catheter of claim 1, wherein the catheter has a proximal end and distal end, and the at least one cavitation hole is aligned with the elongated conductive tube between the proximal end and the distal end.

7. The catheter of claim 1, wherein the at least one cavitation hole comprises rows of cavitation holes.

8. The catheter of claim 1, wherein the catheter is configured to target and break up fibrin.

9. A catheter for use in a lumen of a vascular system, the catheter comprising:
    an emitter assembly comprising at least one emitter that includes a first wire and a second wire such that an uninsulated portion of the first wire and an uninsulated portion of the second wire form an electrode pair configured to generate plasma arcs when voltage pulses are applied across the electrode pair;
    an outermost wall defining an infusion lumen configured to receive a conductive fluid; and
    at least one cavitation hole extending through the outermost wall and opening into the infusion lumen, the at least one cavitation hole being aligned with the electrode pair,
    wherein the electrode pair is positioned in the conductive fluid when the conductive fluid is received in the infusion lumen such that the plasma arcs create a plurality of cavitation bubbles in the conductive fluid, and the at least one cavitation hole is sized and shaped to direct the plurality of cavitation bubbles out of the catheter to a treatment region of the lumen of the vascular system.

10. The catheter of claim 9, wherein at least a portion of the first wire is interleaved with a portion of the second wire.

11. The catheter of claim 9, further comprising a guidewire lumen sized to carry a guidewire, the guidewire lumen extending parallel to the infusion lumen.

12. The catheter of claim 11, further comprising an aspiration lumen separate from and extending parallel to the infusion lumen and the guidewire lumen and at least one port defined in the outermost wall and opening into the aspiration lumen, wherein the at least one port is positioned to receive debris and tissue fragments from the treatment region of the lumen of the vascular system via flow of the conductive fluid.

13. The catheter of claim 12, wherein the at least one cavitation hole has an outer opening located at a first circumferential position on the outermost wall, and the at least one port has an outer opening located at a second circumferential position on the outermost wall spaced apart from the outer opening of the at least one cavitation hole.

14. The catheter of claim 13, wherein the outer opening of the at least one port is larger than the outer opening of the at least one cavitation hole.

15. The catheter of claim 9, wherein the catheter has a proximal end and distal end, and the at least one cavitation hole is aligned with the electrode pair between the proximal end and the distal end.

16. The catheter of claim 9, wherein the at least one cavitation hole comprises rows of cavitation holes.

17. The catheter of claim 9, wherein the catheter is configured to target and break up fibrin.

18. A catheter for use in a lumen of a vascular system, the catheter comprising:
    a plurality of emitters positioned at a location between a proximal end and a distal end of the catheter;
    an outermost wall defining an infusion lumen configured to receive a conductive fluid; and
    at least one cavitation hole extending through the outermost wall and opening into the infusion lumen, the at least one cavitation hole being aligned with the at least one emitter,
    wherein the plurality of emitters are positioned in the conductive fluid when the conductive fluid is received in the infusion lumen and configured to generate a plurality of cavitation bubbles in the conductive fluid when the plurality of emitters are supplied with power to treat a region of the lumen of the vascular system.

19. The catheter of claim 18, wherein the plurality of emitters are configured to generate cavitation bubbles that weaken fibrin.

20. The catheter of claim 19, wherein the plurality of emitters are configured to generate cavitation bubbles that weaken the fibrin through at least one of: collapses, turbulence, and jetting.

21. The catheter of claim 18, wherein the plurality of emitters are configured to generate cavitation bubbles that treat a thrombus.

22. The catheter of claim 18, further comprising an aspiration lumen separate from and extending parallel to the infusion lumen and at least one port defined in the outermost wall and opening into the aspiration lumen, wherein the at least one port is positioned to receive debris and tissue fragments from the treatment region of the lumen of the vascular system via flow of the conductive fluid.

23. The catheter of claim 22, wherein the at least one cavitation hole has an outer opening located at a first circumferential position on the outermost wall, and the at least one port has an outer opening located at a second circumferential position on the outermost wall spaced apart from the outer opening of the at least one cavitation hole.

24. The catheter of claim 23, wherein the outer opening of the at least one port is larger than the outer opening of the at least one cavitation hole.

* * * * *